United States Patent
Maragakis et al.

(10) Patent No.: US 12,217,834 B2
(45) Date of Patent: Feb. 4, 2025

(54) MOLECULAR GRAPH GENERATION FROM STRUCTURAL FEATURES USING AN ARTIFICIAL NEURAL NETWORK

(71) Applicant: D. E. Shaw Research, LLC, New York, NY (US)

(72) Inventors: Paul Maragakis, New York, NY (US); Hunter Nisonoff, New York, NY (US); Peter Skopp, New York, NY (US); John Salmon, New York, NY (US)

(73) Assignee: D. E. Shaw Research, LLC, New York, NY (US)

( * ) Notice: Subject to any disclaimer, the term of this patent is extended or adjusted under 35 U.S.C. 154(b) by 402 days.

(21) Appl. No.: 17/614,856

(22) PCT Filed: May 29, 2020

(86) PCT No.: PCT/US2020/035137
§ 371 (c)(1),
(2) Date: Nov. 29, 2021

(87) PCT Pub. No.: WO2020/243440
PCT Pub. Date: Dec. 3, 2020

(65) Prior Publication Data
US 2022/0230713 A1 Jul. 21, 2022

Related U.S. Application Data

(60) Provisional application No. 62/855,355, filed on May 31, 2019, provisional application No. 62/855,388, filed on May 31, 2019.

(51) Int. Cl.
*G16C 20/30* (2019.01)
*G06N 3/045* (2023.01)
(Continued)

(52) U.S. Cl.
CPC .............. *G16C 20/30* (2019.02); *G06N 3/045* (2023.01); *G06N 3/08* (2013.01); *G16C 20/50* (2019.02); *G16C 20/70* (2019.02); *G16C 20/80* (2019.02)

(58) Field of Classification Search
CPC .......... G06N 3/045; G06N 3/044; G06N 3/08; G06N 5/022; G16C 20/30; G16C 20/70; G16C 20/50; G16C 20/80
See application file for complete search history.

(56) References Cited

U.S. PATENT DOCUMENTS

| | | | |
|---|---|---|---|
| 11,263,534 B1 * | 3/2022 | Prat | G06F 16/951 |
| 11,710,049 B2 * | 7/2023 | Tal | G06N 5/022 |
| | | | 706/45 |
| 2021/0287137 A1 * | 9/2021 | Park | G06N 3/002 |

OTHER PUBLICATIONS

Josep Arús-Pous, Thomas Blaschke, Silas Ulander, Jean-Louis Reymond, Hongming Chen, and Ola Engkvist. "Exploring the GDB-13 chemical space using deep generative models." Journal of cheminformatics, 11(1):20, 2019.
(Continued)

*Primary Examiner* — An H Do
(74) *Attorney, Agent, or Firm* — Occhiuti & Rohlicek LLP

(57) ABSTRACT

Discovering molecules (which may be known or may never have been cataloged or ever synthesized) that have desired characteristics is addressed using a machine learning approach. As compared to a brute-force search of a database of known molecules, which may not be computationally feasible, the present machine learning approach renders identification of both known and unknown molecules computationally tractable. Furthermore, the computational effort is largely shifted to training of the machine learning system using a database of known molecules, and the generation of molecules to match any particular characteristics requires
(Continued)

relatively little computation. The molecules using the present approach may be further studied, for example, with computer-based simulation or after physical synthesis using biological experimentation to ultimately yield useful chemical compounds.

31 Claims, 11 Drawing Sheets

(51) Int. Cl.
  *G06N 3/08* (2023.01)
  *G16C 20/50* (2019.01)
  *G16C 20/70* (2019.01)
  *G16C 20/80* (2019.01)

(56) References Cited

OTHER PUBLICATIONS

Seth D Axen, Xi-Ping Huang, Elena L Caceres, Leo Gendelev, Bryan L Roth, and Michael J Keiser. "A simple representation of three-dimensional molecular structure." Journal of medicinal chemistry, 60(17):7393-7409, 2017.
Hongming Chen, Ola Engkvist, Yinhai Wang, Marcus Olivecrona, and Thomas Blaschke. "The rise of deep learning in drug discovery." Drug discovery today, 23(6):1241-1250, 2018.
Daniel C Elton, Zois Boukouvalas, Mark D Fuge, and Peter W Chung. "Deep learning for molecular design-a review of the state of the art." arXiv preprint arXiv:1903.04388, 2019.
Jesse Engel, Matthew Hoffman, and Adam Roberts. "Latent constraints: Learning to Generate Conditionally from Unconditional Generative Models." arXiv preprint arXiv:1711.05772, 2017.
Justin Gilmer, Samuel S Schoenholz, Patrick F Riley, Oriol Vinyals, and George E Dahl. "Neural Message Passing for Quantum Chemistry." In Proceedings of the 34th International Conference on Machine Learning-Volume 70, pp. 1263-1272. JMLR. org, 2017.
Rafael Gómez-Bombarelli, Jennifer N Wei, David Duvenaud, José Miguel Hernández-Lobato, Benjamín Sánchez-Lengeling, Dennis Sheberla, Jorge Aguilera-Iparraguirre, Timothy D Hirzel, Ryan p. Adams, and Alán Aspuru-Guzik. "Automatic Chemical Design Using a Data-Driven Continuous Representation of Molecules." arXiv:1610.02415v1. ACS Central Science, pp. 1-23. Oct. 11, 2016.
Anvita Gupta, Alex T Müller, Berend JH Huisman, Jens A Fuchs, Petra Schneider, and Gisbert Schneider. "Generative Recurrent Networks for De Novo Drug Design." Molecular informatics, 37(1-2):1700111, 2018.
Sepp Hochreiter and Jürgen Schmidhuber. "Long short-term memory." Neural computation, 9(8):1735-1780, 1997.
Wengong Jin, Regina Barzilay, and Tommi Jaakkola. "Junction Tree Variational Autoencoder for Molecular Graph Generation." arXiv preprint arXiv:1802.04364, 2018.
Anonymous Authors. "Learning Multimodal Graph-to-Graph Translation for Molecular Optimization." arXiv preprint arXiv:1812.01070, 2018.
Artur Kadurin, Sergey Nikolenko, Kuzma Khrabrov, Alex Aliper, and Alex Zhavoronkov. "druGAN: An Advanced Generative Adversarial Autoencoder Model for de Novo Generation of New Molecules with Desired Molecular Properties in Silico." Molecular pharmaceutics, 14(9):3098-3104, 2017.
Yujia Li, Oriol Vinyals, Chris Dyer, Razvan Pascanu, and Peter Battaglia. "Learning Deep Generative Models of Graphs." arXiv preprint arXiv:1803.03324, 2018.
Yu-Chen Lo, Stefano E Rensi, Wen Torng, and Russ B Altman. "Machine learning in chemoinformatics and drug discovery." Drug Discovery Today, vol. 00, No. 00, 2018, pp. 1-9.
Hans Matter and Thorsten Pötter. "Comparing 3D Pharmacophore Triplets and 2D Fingerprints for Selecting Diverse Compound Subsets." Journal of Chemical Information and Computer Sciences, 39(6):1211-1225, 1999.

Stephen Merity, Nitish Shirish Keskar, and Richard Socher. "Regularizing and Optimizing LSTM Language Models." arXiv preprint arXiv:1708.02182, 2017.
Marcus Olivercrona, Thomas Blaschke, Ola Engkvist, and Hongming Chen. "Molecular De-Novo Design through Deep Reinforcement Learning." Journal of cheminformatics, 9(1):48, 2017.
Jane Panteleev, Hua Gao, and Lei Jia. "Recent applications of machine learning in medicinal chemistry." Bioorganic & Medicinal Chemistry Letters, 2018.
Mariya Popova, Olexandr Isayev, and Alexander Tropsha. "Deep reinforcement learning for de novo drug design." Science Advances, 4(7):eaap7885, 2018.
Raquel Rodriguez-Perez, Tomoyuki Miyao, Swarit Jasial, Martin Vogt, and Jürgen Bajorath. "Prediction of Compound Profiling Matrices Using Machine Learning." ACS omega, 3(4):4713-4723, 2018.
David Rogers and Mathew Hahn. "Extended-Connectivity Fingerprints." Journal of chemical information and modeling, 50(5):742-754, 2010.
Benjamin Sanchez-Lengeling and Alán Aspuru-Guzik. "Inverse molecular design using machine learning: Generative models for matter engineering." Science, 361(6400): 360-365, 2018.
Marwin HS Segler, Thierry Kogej, Christian Tyrchan, and Mark P Waller. "Generating Focussed Molecule Libraries for Drug Discovery with Recurrent Neural Networks." ACS central science, 4(1):120-131, 2017.
Marwin HS Segler, Mike Preuss, and Mark P Waller. "Planning chemical syntheses with deep neural networks and symbolic AI." Nature, 555(7698):604, 2018.
Ilya Sutskever, Oriol Vinyals, and Quoc V. Le. "Sequence to Sequence Learning with Neural Networks." In Advances in neural information processing systems, pp. 3104-3112, 2014.
Oriol Vinyals, Alexander Toshev, Samy Bengio, and Dumitru Erhan. "Show and Tell: A Neural Image Caption Generator." In Proceedings of the IEEE conference on computer vision and pattern recognition, pp. 3156-3164, 2015.
Izhar Wallach, Michael Dzamba, and Abraham Heifets. "AtomNet: A Deep Convolutional Neural Network for Bioactivity Prediction in Structure-based Drug Discovery." arXiv preprint arXiv:1510.02855, 2015.
W. Patrick Walters. "Virtual Chemical Libraries: Miniperspective." Journal of Medicinal Chemistry, 62(3):1116-1124, 2018.
R Winter, F Montanari, A Steffen, H Briem, F Noé, and D Clevert. "Efficient Multi-Objective Molecular Optimization in a Continuous Latent Space." ChemRxiv: 7971101, 2019.
Sam Wiseman and Alexander M Rush. "Sequence-to-Sequence Learning as Beam-Search Optimization." arXiv preprint arXiv:1606.02960, 2016.
Dongyu Xue, Yukang Gong, Zhaoyi Yang, Guohui Chuai, Sheng Qu, Aizong Shen, Jing Yu, and Qi Liu. "Advances and challenges in deep generative models for de novo molecule generation." Wiley Interdisciplinary Reviews: Computational Molecular Science, pp. 1-9, 2018.
Stanislaw Jastrzbski, Damian Lésniak, and Wojciech Marian Czarnecki. "Learning to SMILE(S)." arXiv preprint arXiv:1602.06289, 2016.
Peter Pogany, Navot Arad, Sam Genway, and Stephen D Pickett. "De Novo Molecule Design by Translating from Reduced Graphs to SMILES." Journal of chemical information and modeling, 2018.
Evgeny Putin, Arip Asadulaev, Yan Ivanenkov, Vladimir Aladinskiy, Benjamin Sanchez-Lengeling, Alan Aspuru-Guzik, and Alex Zhavoronkov. "Reinforced Adversarial Neural Computer for de Novo Molecular Design." Journal of Chemical Information and Modeling. 2018, 58, 1194-1204.
Winter, Frank Noé, Djork-Arné Clevert. "Neuraldecipher—Reverse-Engineering ECFP Fingerprints to Their Molecular Structures." ChemRxiv, 2020.
Tuan Le, Robin Winter, Frank Noé, and Djork-Arné Clevert. "Neuraldecipher—Reverse-engineering ECFP Fingerprints to their molecular structures" Machine Learning Research, 2020.
Ilya Sutskever, Oriol Vinyals, Quoc V. Le. "Sequence to Sequence Learning with Neural Networks." 2014.

(56) References Cited

OTHER PUBLICATIONS

Paul Maragakis et al. "A deep-learning view of chemical space designed to facilitate drug discovery." Arxiv.org, Cornell University Library, 201 Olin Library Cornell University Ithaca, NY 14853, Feb. 7, 2020, XP081594143.
Kyungdoc Kim et al. "Deep-learning-based inverse design model for intelligent discovery of organic molecules", NPJ Computational Materials, vol. 4, No. 1, Dec. 3, 2018, XP055633998, DOI: 10.1038/s41524-018-0128-1.
Daniil Polykovskiy et al. "Molecular Sets (MOSES): A Benchmarking Platform for Molecular Generation Models", Arxiv.org, Cornell University Library, 201 Olin Library Cornell University Ithaca, NY 14853, Nov. 29, 2018, P081042511.
Yibo Li et al. "Multi-Objective De Novo Drug Design with Conditional Graph Generative Model," Arxiv.org, Cornell University Library, 201 Olin Library Cornell University Ithaca, NY 14853, Jan. 18, 2018, XP081227289.
International Search Report and Written Opinion, PCT Application No. PCT/US2020/035137, mailed Oct. 7, 2020 (13 pages).

\* cited by examiner

MOLECULAR GRAPH GENERATION FROM STRUCTURAL FEATURES USING AN ARTIFICIAL NEURAL NETWORK

CROSS-REFERENCE TO RELATED APPLICATIONS

This application is a national phase under 35 U.S.C 371 of International Application No. PCT/US2020/035137, filed May 29, 2020, which claims the benefit of U.S. Provisional Application No. 62/855,388, filed May 31, 2019, and U.S. Provisional Application No. 62/855,355, filed May 31, 2019. These applications are incorporated herein by reference.

BACKGROUND

This document relates to generating molecular graphs using an artificial neural network, and more particularly to the generation of linear molecular representations that match a vector "fingerprint" or a vector representation of features in three-dimensional space. The features in three-dimensional space may by example correspond to properties of known molecules, or may by example correspond to desirable features that are derived from a pocket in a drug discovery target. Independent of the method for extracting features in three-dimensional space, we will collectively refer to these features as "conformational properties" for the remainder of this document.

Molecules have three-dimensional structures that determine the properties of those molecules, for example, the pharmaceutical activity of those molecules. There exist a number of different representations of small molecules, and each representation has certain advantages and disadvantages for the purposes of molecular design. The most common choice of representation is a so-called "molecular graph," which establishes the covalent connectivity of the atoms and any specified stereochemistry (or lack thereof in the case of racemic mixtures). Such graphs can be represented explicitly by sets of vertices and edges; this particular representation, however, has historically been hard to manipulate effectively using deep learning methods, although some progress in deep learning of generic graphs is currently underway.

A molecular graph can be represented in a linear symbolic form. For example, the simplified molecular-input line-entry system (SMILES) is a specification in the form of a linear notation for describing a molecular graph. SMILES representations of molecules have been used successfully in deep learning models that generate molecules. A SMILES string is advantageous because it encodes an exact structural representation of a molecule, but molecules with only small chemical differences can have very different SMILES strings, making them poor representations of chemical similarity and thus difficult to use to tailor molecular properties.

Typically, a number of equally valid SMILES strings can be written for a molecule. For example, CCO, OCC and C(O)C all specify the structure of ethanol. Algorithms have been developed to generate the same SMILES string for a given molecule; of the many possible strings, these algorithms choose only one of them. Very generally, a graph-based computational procedure can be used to generate a SMILES string by printing the symbol nodes encountered in a depth-first tree traversal of a chemical graph. The chemical graph is first trimmed to remove hydrogen atoms and cycles are broken to turn it into a spanning tree. Where cycles have been broken, numeric suffix labels are included to indicate the connected nodes. Parentheses are used to indicate points of branching on the tree. The resultant SMILES formed depends on the choices of the bonds chosen to break cycles, of the starting atom used for the depth-first traversal, and of the order in which branches are listed when encountered. Atoms are represented by the standard abbreviation of the chemical elements, in square brackets (except in some cases for a subset of common atoms). Various types of bonds are represented by symbols including . - = # $ : / and \.

Another type of representation of a molecule relates to the presence of particular elements or substructures. For example, a "structural key" may comprise values of a fixed number of Boolean values, for example, represented in a bit vector in which each position in that bit vector is assigned to a specific element or substructure. Given a molecule's structure, for example, as specified by a SMILES linear form, the values of each of the bits of the structural key can be determined, thereby yielding the module's key.

Another representation of features of a molecule is as a vector "fingerprint." Such a fingerprint may be represented as a bit vector, however the bit vector is not positional in the sense that each position is associated with a different element or substructure. Rather, for each attribute from a set of attributes (e.g., substructures etc.), a corresponding set of one or more bits is set, for example, with a pseudo-random assignment of the bits for each attribute. Therefore, to determine if a molecule may have a desired number of attributes, all the bits of those attributes must be set. In some cases, these bits may be set with hopefully low probability as a result of other attributes being present. The fingerprint may be considered as a form of hash function of the molecular graph, or as the logical OR of hash functions of the attributes and substructures present in the molecule. One type of fingerprint is referred to as an "extended connectivity fingerprint," which encodes the local chemical environment around a molecule's heavy atoms. Chemically similar molecules generally have similar extended connectivity fingerprints, and this advantage over the SMILES representation has led to fingerprints being commonly used as the molecular representation in computer codes that evaluate chemical properties, or that search for similar molecules in a database. As opposed to SMILES, however, a fingerprint is a structurally lossy encoding of a molecule: a given fingerprint does not always correspond one-to-one with a single molecule, and furthermore the task of generating molecular graphs from a fingerprint has historically been a significant problem, making it infeasible to take advantage of the ability to tailor the chemical properties of fingerprints in order to develop improved molecules.

For a library of molecular graphs, it is possible to generate corresponding structural keys or fingerprints. There are a number of high-quality chemistry libraries available, including eMolecules, molPort, and SureChEMBL. When one wishes to identify molecules in such a library with a set of desired attributes, a search of all fingerprints for the molecules in the library can be undertaken to identify the corresponding molecular graphs.

However such a search has several difficulties, including the computational expense of conducting the search of the database, which may have an extremely large number of molecules to analyze (e.g., more than a billion molecules for some databases). Furthermore, such a search-based approach lacks a way of generating molecular graphs that may not have corresponding entries in the database. That is, such techniques do not generate new molecules.

Some researchers have attempted to process SMILES representations of molecules to generate fingerprints or other vectors representing chemical properties (e.g., toxicity, activity, solubility), for example, using recurrent neural networks (RNN) and techniques previously applied in natural language (i.e., text) processing (NLP). For example, in natural language processing, Long Short-Term Memory (LSTM) Recurrent Neural Networks (RNNs) have been used to predict a next word based on the sequence of preceding word to generate random sentences, or similarly, determine the probability of the next word conditioned on the sequence of preceding words to yield a probability of a particular sentence. In application to molecule generation, researchers have used the symbols in a SMILES representation in the place of words in the NLP context, thereby allowing generation of molecules. A particular form of LSTM network that has been found useful in NLP applications is referred to as an Averaged Stochastic Gradient descent (ASG) training with Weight Dropping (together AWD) LSTM. Yet other researchers have used variational autoencoders that accept and predict SMILES representations, with each molecule corresponding to a vector in a latent space, a latent vector, that is discovered during training on a library of known molecules. Such a latent vector has been used to predict properties of the corresponding molecule. However, although such a latent space may be effective in compressing a molecular representation, it is not necessarily well-structured to be related to the properties of the molecule. Furthermore, such automated generation of fingerprints does not address the problem of determining a SMILES representation from fingerprint or other representation of a molecule's attributes or properties. Some researchers have also applied NLP techniques to generate random molecule representations using RNNs that are trained on a corpus of known molecules, for example, a corpus of molecules that have a desired property. However, such approaches require that the training corpus with the desired property be available, and does not extend to specific properties that may represent a combination of a set of attributes or substructures.

In natural language processing, sequence-to-sequence models have been used to map a word sequence in one language to a word sequence in another language. For example, an LSTM structure is used to process the input sequence from beginning to end. This yields a value of a state vector in the LSTM that represents that input sequence. This state vector is then used as the initial state for an LSTM that generates the output sequence. Related techniques have been used to generate text captions directly from images.

SUMMARY

In a general aspect, the technical problem of discovering molecules (which may be known or may never have been cataloged or ever synthesized) that have desired characteristics is addressed using a machine learning approach. As compared to a brute-force search of a database of known molecules, which may not be computationally feasible, the present machine learning approach renders identification of known or not previously known molecules computationally tractable. Furthermore, the computational effort is largely shifted to training of the machine learning system using a database of known molecules, and the generation of molecules to match any particular characteristics requires relatively little computation. The molecules discovered using the present approach may be further studied, for example, with computer-based simulation or after physical synthesis using biological experimentation to ultimately yield useful chemical compounds. A deep learning approach translates structural features, such as fingerprints or conformational properties, to molecular structures, such as molecular graphs or linear representations of such graphs (e.g., encoded as SMILES strings). Although the mapping from structure to structural features may be deterministic or easily computed, in general such mappings are "lossy" and/or "non-invertible" in the sense that the inverse mapping from structural features to molecule structure is non-deterministic and difficult to compute. The present approach provides a way of computing such an inverse mapping by accepting as input the structural features and generating a best match to the input structural features or an ordered list of a set of top matches. In some embodiments, the approach further provides additional fine-tuning by using structural features of an input molecule to propose modified molecules that are both chemically valid and have improved properties of interest as compared to the input molecule.

At least some embodiments operate by generating a series of small molecules that are chemically related to a given small-molecule input. In one example, the system takes a molecular fingerprint as input and translates the fingerprint to a sequence of SMILES strings in order of an estimated probability of matching the fingerprint, starting with the most likely one. In one use of the approach, the neural network is modified with transfer learning (i.e., learning of downstream tasks with additional training on small, specialized datasets), and then proposes a sequence of molecules that are chemically similar to the input but are likely improved for specified properties of interest.

In one aspect, in general, a computer-implement method is used to generate a molecular graph based on a data representation of first structural features of a first molecule (e.g., of an unknown target or known reference molecule). The data representation of the first structural features of the molecule are processed using a computer to yield a first latent representation of the first molecule. Then, the first latent representation is processed to yield a data representation of a molecular graph of at least one molecule matching the first structural features (e.g., corresponding to a target molecule), and optionally a set or sequence of molecular graphs of respective molecules matching the first structural features (e.g., a sequence of target molecules ordered by a degree of match).

Aspects may include one or more of the following features.

The molecular graph of the at least one molecule is provided for evaluation of chemical or biological properties of said at least one molecule.

The data representation of the first structural features is obtained by processing a data representation of a first molecular graph (e.g., a molecular graph of a reference molecule) to yield the first structural features.

Processing the data representation of the first molecular graph comprises applying a plurality of rules to yield the first structural features.

The data representation of the molecular graph of the at least one molecule comprises a linear symbolic representation. For instance, the linear symbolic representation corresponds to a SMILES representation. The linear symbolic representation may comprise symbols each representing at least some individual atoms and symbols each representing a group of bonded atoms. The linear symbolic representation may comprise a compression of the SMILES representation.

The first structural features comprise at least one of (a) a fingerprint determined from a molecular graph, and (b) conformational properties of a conformation of a molecule. The conformational properties may be determined for a known reference molecule. The conformational properties may be determined as desired in an unknown target molecule, for example, representing features that are derived from a pocket in a drug discovery target.

The fingerprint comprises a fixed length binary vector, for instance comprising an extended connectivity fingerprint.

The fingerprint representation is encoded to a continuous vector.

The representation of conformational properties comprises properties tied to three-dimensional locations of those attributes in a conformation of a molecule (e.g., in a conformation of a desired molecule).

The conformational properties comprise a set of locations and discrete categories of properties of a molecule at said locations.

The conformational properties comprise conformational properties of a plurality of low-energy conformations of a molecule (e.g., in a conformation of a desired molecule).

The processing of the data representation of the first structural features to yield the first latent representation of the desired molecule comprises using a first artificial neural network (e.g., a deep neural network, DNN).

The processing the first latent representation to yield the data representation of the molecular graph of at least one molecule matching the first structural features comprises processing the latent representation using a second artificial neural network (e.g., a recurrent neural network, RNN) to yield a sequence representation of the at least one molecule matching the structural features.

The processing of the latent representation to yield the sequence representation of the at least one molecule matching the structural features comprises processing the latent representation to yield a plurality of sequence representations, determining structural features for each of said sequence representations, and comparing the determined structural features to determine a match of the determined structural features to the first structural features.

The processing of the latent representation to yield the plurality of sequence representations includes generating a first sequence representation, and wherein generating the first sequence representation includes generating successive distributions of next symbols in the sequence representation using the latent representation as an input to a second artificial neural network and searching possible sequences using the successive distributions to yield one or more best sequences.

Generating a distribution of a next symbol includes using the latent representation and a prefix of the next symbol in the sequence as input to the second artificial neural network.

Searching the possible sequences comprises performing an A-star search procedure.

In another aspect, in general, a computer-implemented method is used to train a neural network for generating a molecular graph. A first set of molecular graphs is obtained. Each of the molecular graphs is processed to determine a respective sequence representation. Each of the molecular graphs is also processed to determine respective structural features. A combination of a first neural network and a second neural network is trained using the structural features and respective sequence representations. The first neural network implements a transformation from the structural features and a latent feature representation, and the second neural network implements a transformation from the latent feature representation to a sequence representation.

Aspects may include one or more of the following features.

The structural features comprise fingerprints.

A second set of molecular graphs is obtained. Each molecular graph of the second set of molecular graphs is processed to determine respective latent representations. Each molecular graph of the second set of molecular graphs is also processed to determine respective conformational properties. A third neural network is trained using the latent representations and the conformational properties. The third neural network implements a transformation from conformational properties to a corresponding latent representation. A combination of the third neural network and the second neural network together implement a transformation from conformational properties to a sequence representation of a molecular graph.

A set of pairs of molecular graphs is obtained, each pair having a first molecular graph and a second molecular graph, the second molecular graph representing a second molecule having a different (e.g., a greater or alternatively a lesser) degree of a property than a first molecule represented by the first molecular graph. The first molecular graphs are processed to determine corresponding first structural features. A transfer learning procedure is applied to the second neural network using the pairs of first structural features and second molecular graphs.

The methods for training the neural network (i.e., the combinations of first, second, and/or third neural networks, which comprise an overall neural network) is used to train neural networks used in the computer-implemented processing of structural features to yield a molecular graph according to the methods set forth above.

Advantages of one or more approaches outlined above include increased utility (e.g., accuracy, quality) in discovering molecules. Furthermore, the approaches may discover previously unknown molecules with desired properties. The computational cost of transforming desired features to output molecules are vastly reduced as compared to an exhaustive search, which may not be computationally feasible given the size of today's small molecule databases. Other features and advantages are apparent from the description below and from the appended claims.

DETAILED DESCRIPTION

Notation

Figure 1:
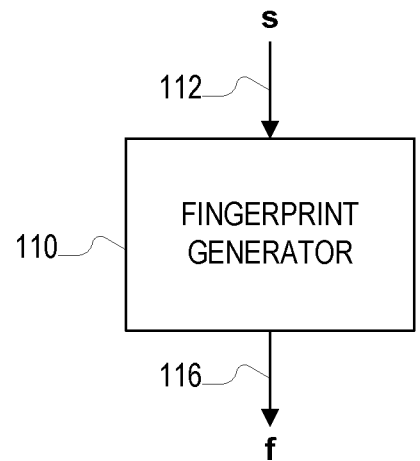
FIG. 1 is a diagram representing fingerprint generation from a SMILES string.

In general, the following notation is used in the description below:

f a fingerprint for a molecular graph, with $f^{(n)}$ being the fingerprint for the $n^{th}$ molecule in a database of molecules.

l a latent representation of a molecule.

s a sequence representation of a molecular graph (e.g., SMILES), with $s_t$ being the $t^{th}$ symbol in the sequence.

p a probability distribution over possible symbols.

$r_i$ a recurrent state after processing the first t symbols of a sequence.

y a representation of properties of one or more molecular conformations.

P(x) the probability of x, with P(x|z) being the probability of x conditioned on z.

Fingerprint to SMILES Processing

Very generally, Artificial Neural Network (ANN) techniques, including for example, Recurrent Neural Network (RNN), transformer network, or graph neural network techniques are used in one or more embodiments described below to process structural features for a molecule (e.g., functions of a molecular graph of the molecule, referred to as "fingerprints," and/or functions of one or more conformations of the known or desired molecule, referred to as "conformational properties") and output one or more SMILES molecule representations that are consistent with or guided by the structural features. In this section, an approach to processing fingerprints is described, while in a subsequent section, an approach to processing conformational properties is described. In some aspects, the techniques extend approaches used in Natural Language Processing (NLP) to the problem of targeted SMILES generation. Rather than generating random SMILES representations, for example, matching a distribution induced by a training corpus of exemplary molecules, the present techniques are targeted to a specific fingerprint or other specification of desired attributes of the resulting molecules.

SMILES Compression

Before continuing with the description of the processing of a SMILES representation, preferably although not essentially, each SMILES representation is transformed into a compressed SMILES representation, referred to here as cSMILES. This compression is invertible so that if a cSMILES representation of a desired molecule is generated, this compressed form can be deterministically expanded into a standard SMILES form. In the compression approach described below, at least some of the symbols in the cSMILES representation may represent a frequently occurring arrangement of atoms (e.g., a subsequence of bonded atoms, a ring, etc.) corresponding to a substring of a SMILES representation.

One way of implementing the invertible (i.e., lossless) compression of the SMILES representations is to use byte-pair encoding (BPE). In BPE compression, a set of valid sequences, in this case SMILES strings, are analyzed to find the most frequently occurring pairs of characters. Each such pair of characters is assigned a new symbol, and all occurrences of that pair are replaced with that symbol, thereby reducing the lengths of at least some of the strings. This BPE compressed symbol serves the role of a character in a second analysis, where the most frequent pair of letters (or added symbols) is replaced with a further new BPE compressed symbol. This process is repeated until an ending criterion is met, for example, when a total number of original characters and added symbols reaches a desired size, or a desired compression is achieved. For example, a single symbol may represent subsequences such as Cc1nn, (C) or c(0, which may represent a group of bonded atoms.

Without any BPE compression, the lengths of typical SMILES representations in a database of about 10 million drug-like small molecules are approximately in the range 24 to 72 characters (5th and 95th percentiles, respectively). When the total number of available characters and added symbols is increased to 1000, the representations are in the range 5 to 19 characters/symbols, and when the total is increased to 8000, the representations are in the range 3 to 15 characters/symbols. In the 8000 character/symbol case, 26 symbols cover 99.99% of the representation symbols. As will become apparent in the description of the sequence decoder, compression not only reduces computational requirements but may also increase the robustness of the generation by forming the generated SMILES representations with frequently occurring substrings.

In addition, explicit markers are used to denote the start and end of a string, for example, using a <begin> and an <end> symbol. As discussed further below, in some examples, generated cSMILES strings are constrained to begin with the <begin> symbol, while in other examples, the generated strings may be generated in reverse starting with <end> and terminating with <begin>.

An example of alternative marking of the start and end of a string is <begin> <forward>, $s_2, s_3, \ldots, s_{n-1}$, <end> for molecules written from left to right, and <begin> <reversed>, $s_{n-1}, \ldots, s_3, s_2$, <end> for molecules written from right to left.

Model Structure

Referring to FIG. 1 a molecular graph s 112, which may be string of length N, may be transformed into a "fingerprint" f 116 comprising a set of binary values by a fingerprint generator 110. This process may be automated, for example, by specifying a set of chemical rules to apply to the structure s to determine whether corresponding predetermined patterns are found in the structure, and if so, corresponding bit values are set in the fingerprint. For example, a fingerprint may comprise a vector of 4,096 binary values. Although it may be straightforward to generate a fingerprint using chemical rules from the representation of the molecular graph, for example, a SMILES representation, finding the inverse is not as straightforward. Therefore there is no effective method of generating one or more molecules that exactly or approximately match a fingerprint.

Figure 2:
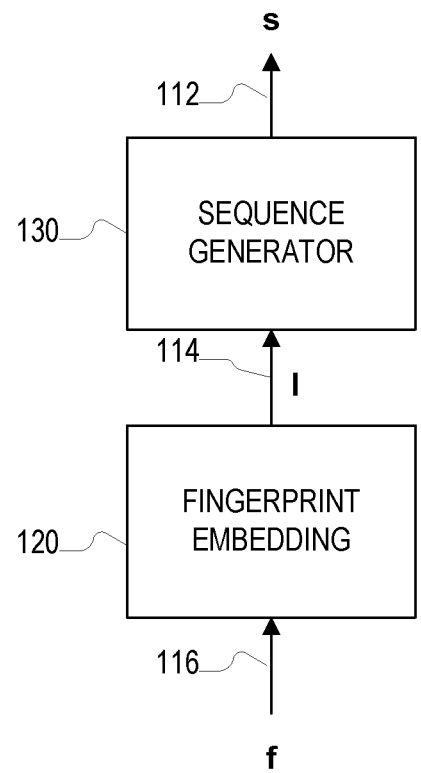
FIG. 2 is a diagram representing inversion of a fingerprint to generate a SMILES string.

Referring to FIG. 2, very generally, an approach to exact or approximate "inversion" of the fingerprinting accepts a fingerprint f 116 and transforms that fingerprint into a "latent" representation l 114 via a latent feature generator 120. For example, the latent feature space may comprise a real-valued vector with 800 elements. The latent representation l is then passed to a sequence generator 130. In some implementations, the sequence generator 130 outputs a representation ŝ 112 of a single molecule. In other implementations, not illustrated in FIG. 2, the sequence generator outputs a set of possible representations $\{s_i\}$, and these representations are optionally ranked or associated with corresponding probabilities $\{P(s_i)\}$. The ranking or probability generally indicates the degree of match of the structure to the fingerprint.

Note that if a fingerprint is generated using the process illustrated in FIG. 1 with a molecular graph generated by the process shown in FIG. 2, there is no guarantee that the original fingerprint will be regenerated. However, even if the molecules do not yield the identical fingerprint, the molecules may nevertheless have desired properties.

Continuing to refer to FIG. 2, in at least some embodiments the fingerprint embedding 120 is implemented as a feedforward neural network, while the sequence generator 120 makes use of a Recurrent Neural Network (RNN).

Figure 3:
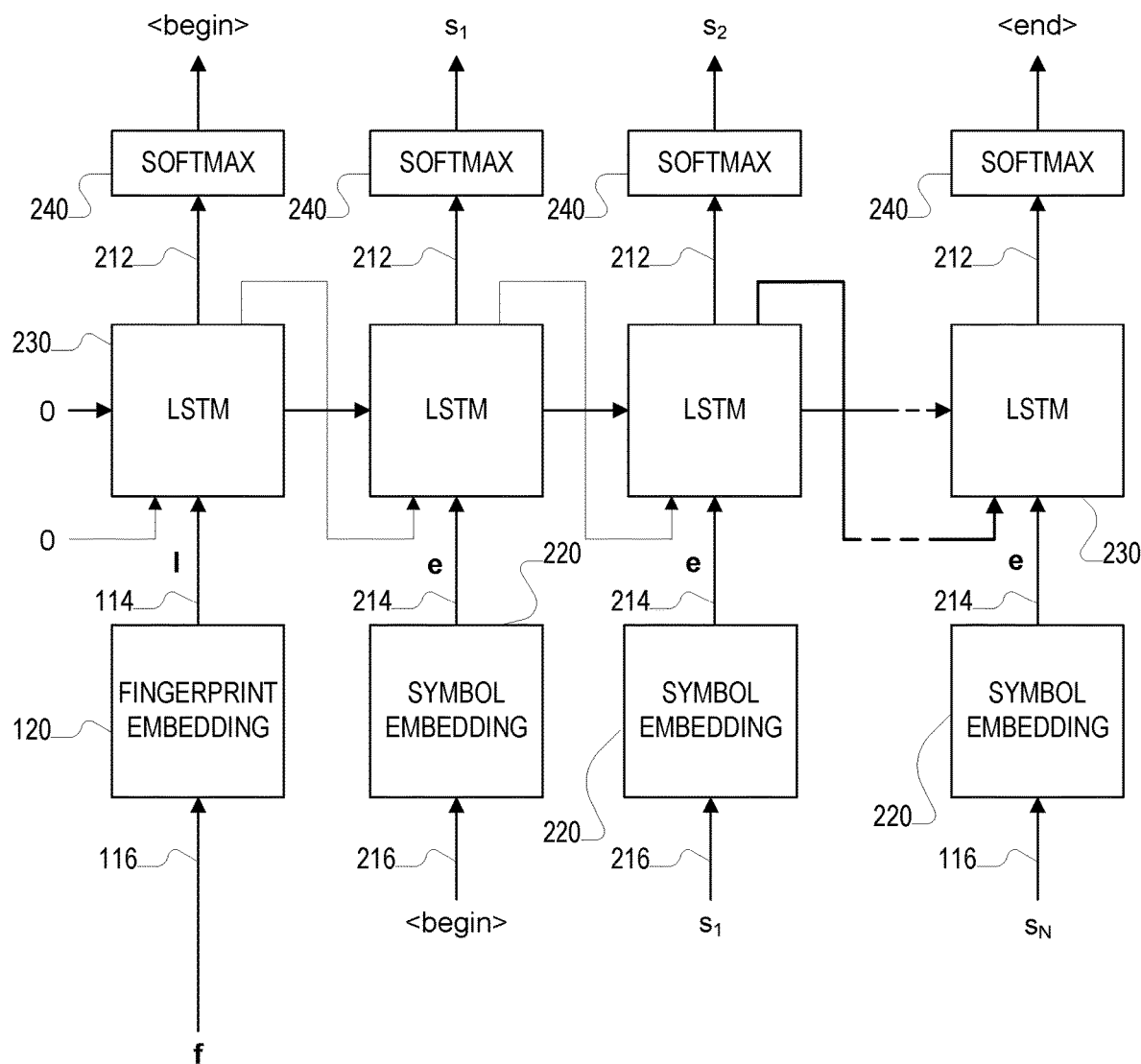
FIG. 3 is a neural network for fingerprint-to-sequence generations.

Referring to FIG. 3, an embodiment of the approach shown in FIG. 2 makes use of a Long Short-Term Memory (LSTM) RNN. In the LSTM structure of the sequence generator, an LSTM cell 230 is used to generate successive symbols of the output sequence. In the figure, there are multiple instances of the LSTM cell 230 illustrated, with each instance corresponding to a different iterative application of a single cell. The "unrolling" of the instances over time is provided for exposition and does not correspond to implementation with multiple separate cells.

In the figure, time goes from left to right. The link between adjacent LSTM cells 230 illustrates a memory that is maintained in the cell between successive times, and in the unrolled representation in the figures, represents the transfer of the memory value from being generated by the LSTM cell at one time for use by the LSTM cell at the next time. Therefore each LSTM cell 230 in the figure has a memory output and a memory input (except for the leftmost cell, which defaults to a zero-value memory input). The memory value is represented as a vector of real values. In general, this memory vector has a different number of entries than the latent representation.

Each LSTM cell 230 receives an input value, in the figure represented as an input on the bottom edge of the cell, and produces an output, represented in the figure as emitting from the top edge of the cell. In some implementations, the inputs and outputs of the LSTM cells are real-valued vectors with 800 elements. The first (leftmost) LSTM cell 230 receives an input l 114 (an 800-value vector) that is determined from the input fingerprint f 116 by the fingerprint embedding 120. The subsequent LSTM cells receive inputs that are based on the immediately prior symbol that is generated. The outputs of the LSTM cells 230 pass through a "softmax" transformation, which is a feedforward neural network that receives the vector of 800 output values and generates 8000 output values representing the probabilities of the 8000 possible symbols of the cSMILES representation. In some examples, the symbol with the highest output value (i.e., highest probability) is selected as the output symbol in the sequence. As described further below, alternative approaches do not make hard decisions (i.e., decisions that are not revisited) at each position in the sequence and rather perform a search over possible sequences to determine one or more sequences based on their overall match to the fingerprint (i.e., an overall probability as described below).

In FIG. 3, the first instance of the softmax transformation yields the symbol <begin> as the highest probability symbol. In the description below, this first symbol in the sequence is denoted $s_0$. The symbol value $s_0$ is provided as input to the first instance of a symbol embedding 220. There are various ways to implement the symbol embedding, including as a neural network that receives a "one-hot" representation of the symbol, or as a lookup table indexed by the symbol. Each subsequent symbol $s_1, s_2, \ldots, s_N$ can be generated in this manner, until a final symbol $s_{N+1}$=<end> is generated, indicating the end of the cSMILES sequence, which is then expanded to form the full SMILES form.

Figure 4:
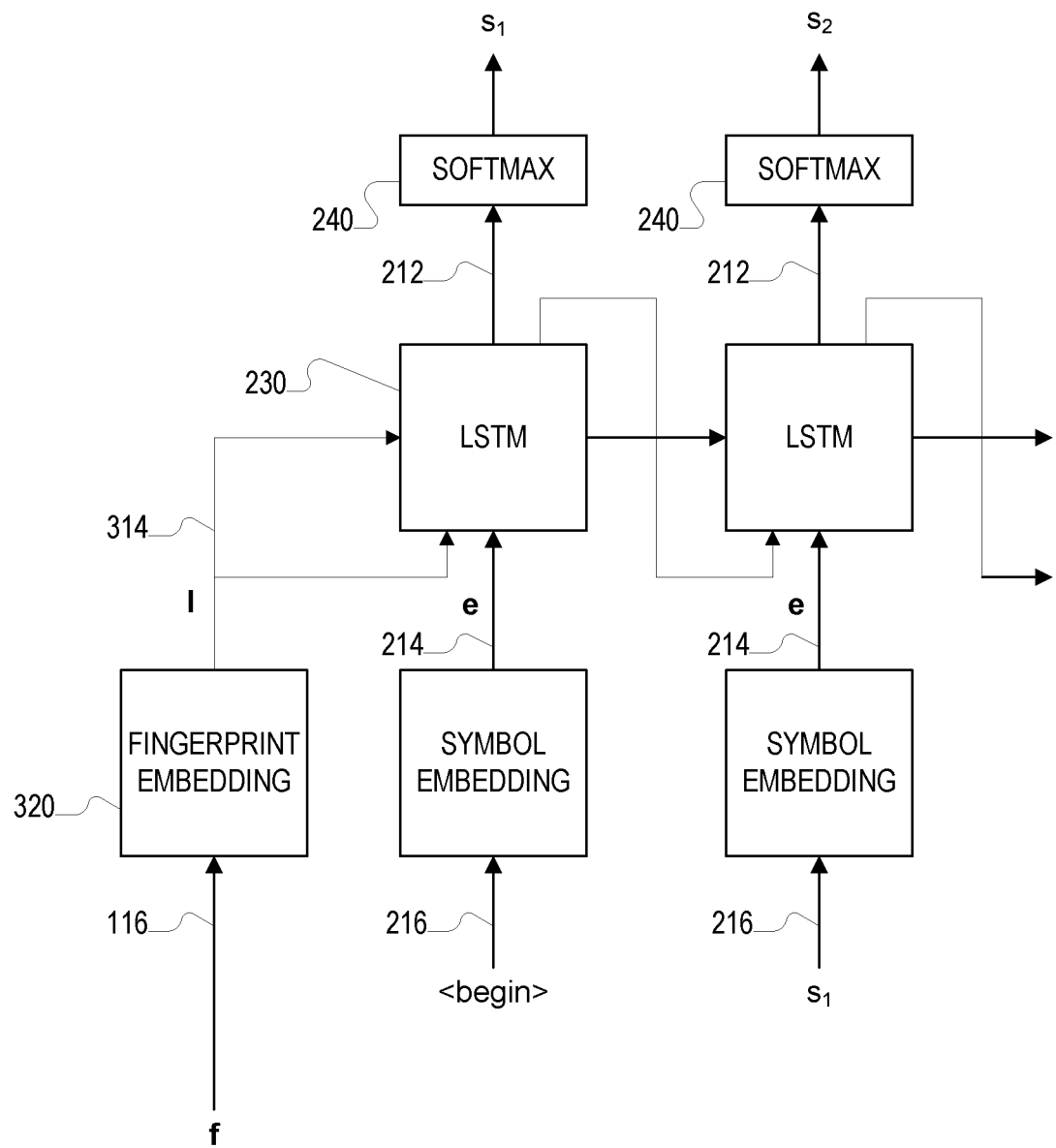
FIG. 4 is an alternative neural network configuration for fingerprint-to-sequence generations.

Referring to FIG. 4, an alternative arrangement does not make use of the first LSTM cell 230 shown in FIG. 3. Rather, an alternative fingerprint embedding 320 transforms the fingerprint f 116 to provide the initial values of the LSTM cell state and the hidden input. That is, the output of the fingerprint embedding 320 is a real-valued vector of the dimension of the memory of the LSTM cells plus the dimension of the hidden input. The fingerprint embedding passes its output directly to the first LSTM cell. The <begin> symbol is provided as input 216 to the first symbol embedding 220 to provide input to the first LSTM cell 230.

Figure 5:
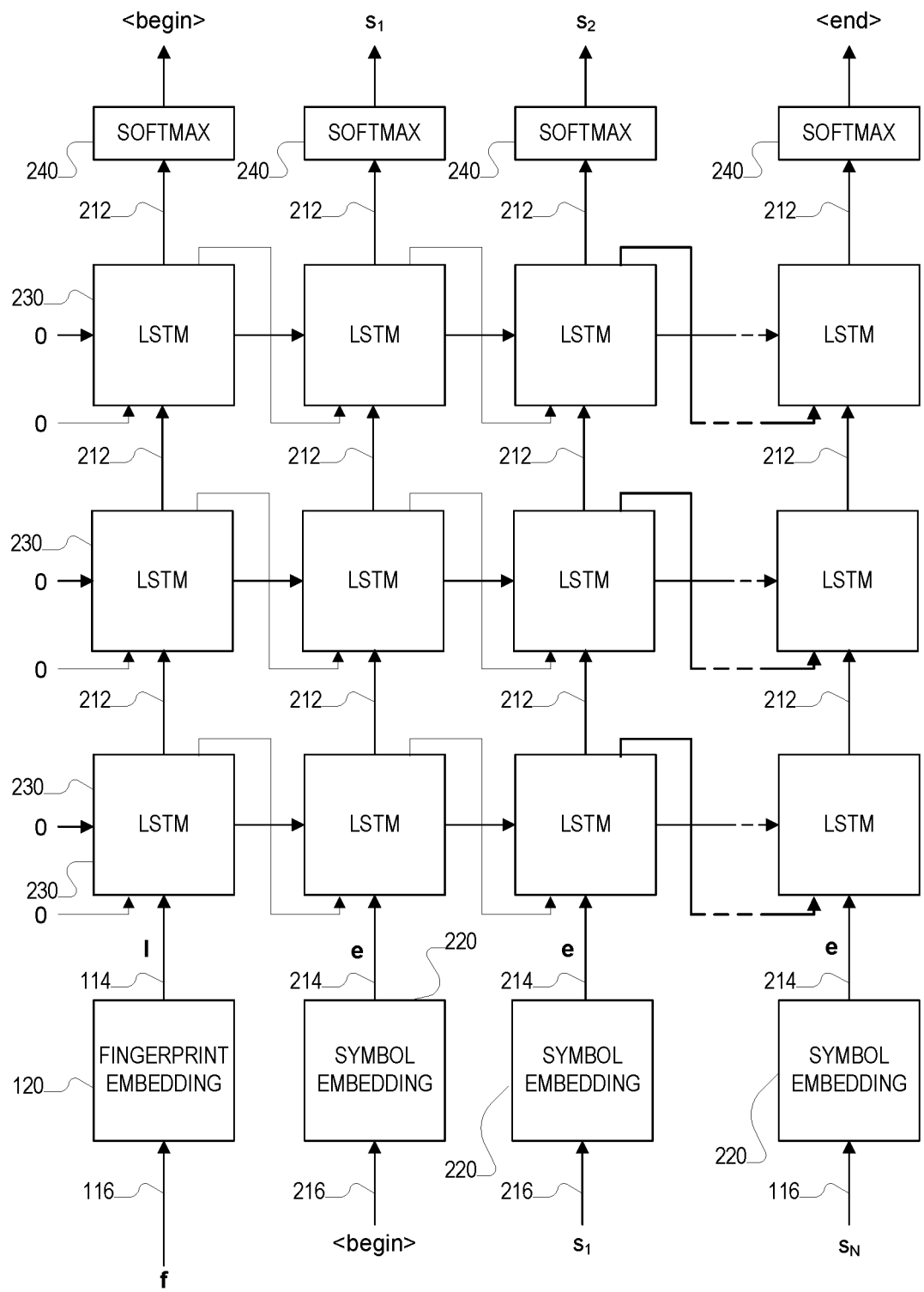
FIG. 5 is a deep neural network configuration for fingerprint-to-sequence generations.

Referring to FIG. 5, in some implementations, a deep LSTM structure is used. In such a structure, illustrated in FIG. 5 "unrolled" over time, each time instance of LSTM cell 230 at a particular level retains its state and uses the hidden output from the previous time at that same level as an input. Various depth of structure may be used, for example, 2 or more and/or 6 or fewer layers, and preferably in a range of 3 to 5 layers. Note that as illustrated, at the first (left-most in the figure) LSTM cells 1230, both the state and the hidden inputs are initially zero.

Sequence Probability

Rather than selecting each symbol based on its individual highest probability, the overall probability $P(s|f)$ of the entire sequence can be considered. Consider an N+1 long sequence with $s_0$=<begin> and $s_{N+1}$=<end>. The probability of this sequence can be decomposed as $$P(s_0, \ldots, s_{N+1} \mid f) = P(s_0 \mid f) P(s_1 \mid s_0, f) \qquad (1)$$
$$P(s_2 \mid s_0, s_1, f) \ldots$$
$$P(s_N \mid s_0, \ldots, s_{N-1}, f)$$
$$P(s_{N+1} \mid s_0, \ldots, s_N, f)$$
$$= P(s_0 \mid f) \prod_{t=0}^{N} P(s_{t+1} \mid s_0, \ldots, s_t, f) \qquad (2)$$

Each of the terms in equations 1 and 2 corresponds to the output of the softmax 240 for one of the times t=0 to t=N+1. In the network form shown in FIG. 4 the term $P(s_0|f)=P(<begin>|f)$ can be ignored as being equal to 1.0.

If given a particular sequence s the probability of that sequence may be evaluated by a sequence of N+1 LSTM cells 230 producing the probabilities that are multiplied together to form the overall probability.

Sequence Search

As introduced above, selection of the symbol at each time in turn may not yield an overall sequence with the highest possible probability.

A variety of search algorithms may be used to find an optimal sequence representation $$s^{(opt)} = \arg\max_s P(s \mid f) \qquad (3)$$

Referring to FIGS. 6 through 9, an A* (A-star) procedure is used in which the search can be considered to be a tree search in which each node represents a prefix of the sequence representation of a molecule. Each node has links to its children, with one link for each possible next symbol, with a link probability being the conditional probability of that next symbol conditioned on the prefix.

Figure 6:
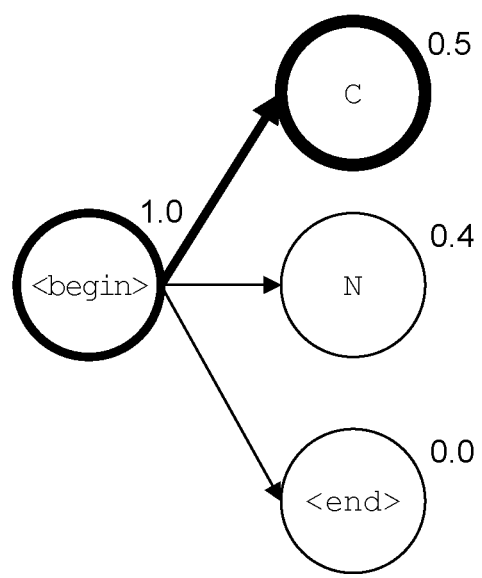
FIG. 6 is an initial search tree.

In FIG. 6 a root node labeled <begin> has probability 1.0. The second symbols in the sequence have been generated, illustrated here as symbols C, N, and <end>, with probabilities 0.5, 0.4, and 0.0 respectively (other symbols with a cumulative probability mass of 0.1 are not illustrated—at any point in time the sum of the probabilities of all possible leaves should be 1.0).

One approach to searching for the highest probability sequence is to build the tree incrementally by extending the leaf that has the currently highest probability. In FIG. 6, the node labeled C (indicated in bold), corresponding to the prefix (<begin>,C) is extended.

Figure 7:
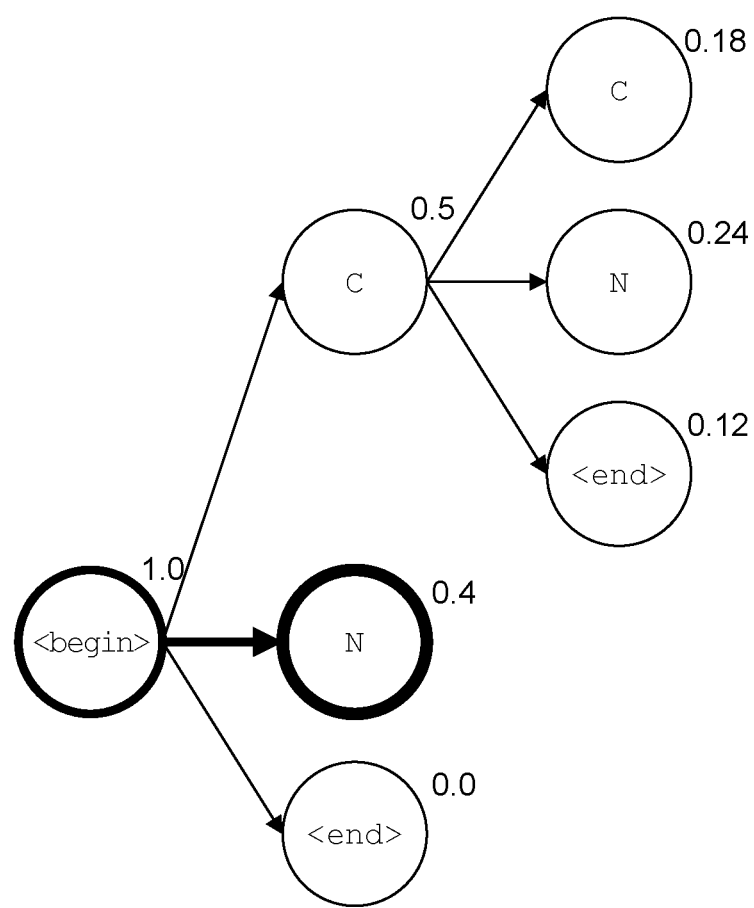
FIG. 7 is the search tree after one iteration.

Referring to FIG. 7 three additional nodes are shown, corresponding to the prefixes (<begin>,C,C),(<begin>,C,N), and (<begin>,C,<end>). The probabilities indicated, 0.10, 0.24, and 0.12 represent the product of the probabilities output from the softmax layers of the recurrent neural network shown in FIG. 3. After adding the new nodes, an already existing node corresponding to the prefix (<begin>, N) has the highest probability of all leaves at 0.4.

Figure 8:
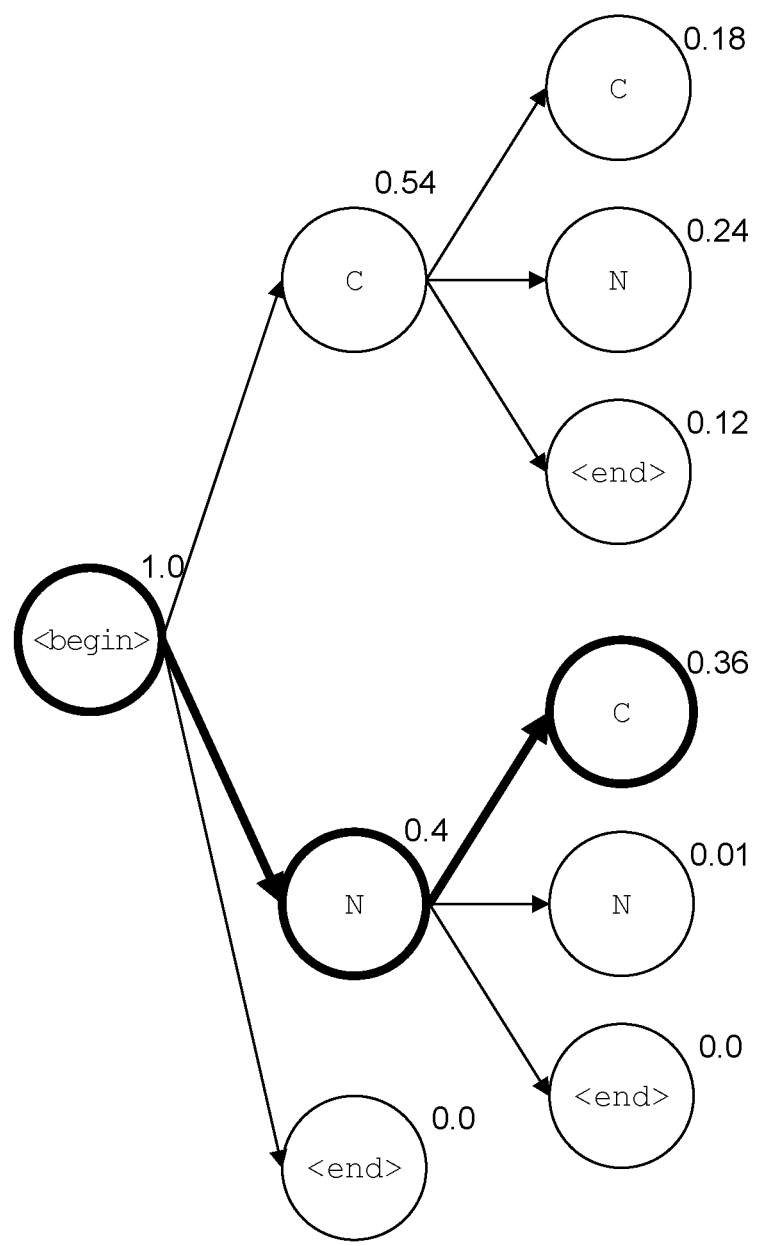
FIG. 8 is the search tree after two iterations.
Figure 9:
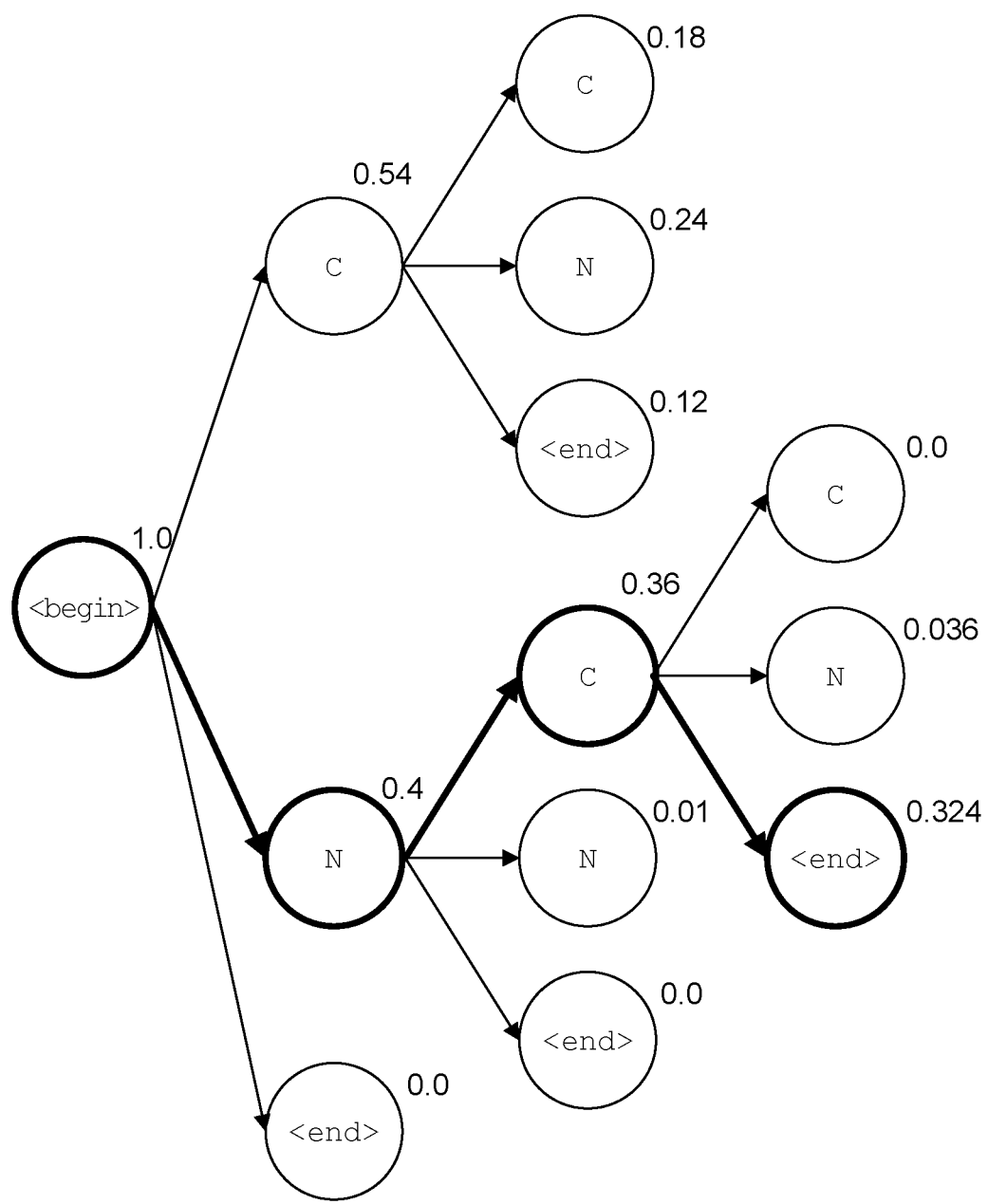
FIG. 9 is the search tree after identification of a complete sequence.

Referring to FIG. 8, the node with probability 0.4 is extended, and the new node corresponding to the prefix (<begin>,N,C) has the highest probability at 0.36. FIG. 9 shows the extension of that node, yielding a highest probability node corresponding to the full sequence (<begin>, N,C,<end>) with probability 0.324. Because no other leaf has a probability greater than 0.324, no extension of those leaves could yield an overall sequence with lower probability, and therefore the search is complete. More generally, the first <end> located does not necessarily correspond to the optimal solution. Any other leaf that has a probability greater than the highest probability of a complete sequence has the potential of yielding a better result, and therefore the iteration continues with such nodes. Ultimately, there are no suitable nodes to extend, and the optimal sequence is guaranteed to have been found.

In some uses of this approach, rather than finding only the single highest probability sequence, it may be desirable to find an "N-best" list of sequences, for example a list of the sequences with the highest probabilities, or a list of sub-optimal sequences that have probabilities within a certain factor of the highest probability sequence. In such cases, the search may be continued after the optimal sequence is found, for example, by extending leaves of the tree that have corresponding probabilities within a factor of the optimal probability.

Training

Each of the neural network components shown in FIG. 3 is parameterized and values of these parameters (often referred to as "weights") are determined using an iterative optimization approach according to an overall loss function characterizing the degree of match of the parameterized system and a training corpus. The training corpus of N molecules includes (fingerprint, sequence) pairs:

$$\{(f^{(n)}, s^{(n)}), n=1, \ldots, N\}. \qquad (4)$$

As is conventional in training of recurrent neural networks, for each training sequence, the "unrolled" structure is used with each instance of the components having the same parameter values. Although a variety of parameter estimation or fitting techniques could be used, a preferred approach is to use a stochastic gradient descent approach, and in particular to use averaging and weight dropping. This approach is referred to as AWD. A preferred criterion for optimizing the parameters is a cross-entropy loss function, which essentially maximizes the probabilities (i.e., their product across the database of training molecules) of the true sequences $s^{(n)}$ given their fingerprints $f^{(n)}$.

It should be recognized that the because of the concurrent training of the fingerprint embedding 120 and the sequence generator 130, a byproduct of the training is that each molecule in the corpus is further characterized by its latent representation. Therefore, after training is completed, the training library can be augmented with these latent representations $$\{(f^{(n)}, s^{(n)}, l^{(n)}), n=1, \ldots, N\}. \qquad (5)$$

Because the inputs to the symbol embedding components 220 are discrete values (e.g., values chosen from the discrete set of 8000 cSMILES symbols), these components may be implemented as lookup tables (LUT), and the training procedure essentially determines the values in these tables.

In a variant of the training procedure, after performing the training on a large number of fingerprints f and their corresponding sequences s, a limited amount of additional training (e.g., a limited number of iterations using a limited number of training pairs) is performed in an approach that may be referred to as "transfer learning." In this transfer learning, pairs of molecules (A, B) are used to fine-tune the parameters of a pre-trained network. Molecule B of each pair is chosen to be "better" in a particular sense than the corresponding molecule A, but otherwise is similar. An example of a sense that the molecule B's of the pairs are better than the A's is that the B molecules are less toxic in the context of drug discovery than the corresponding A's. Another example is that the B molecule binds better with a particular receptor site. The B molecules may be better in one or more of a variety of aspects, while generally remaining similar to the corresponding A molecules. The A molecule has a fingerprint $f^A$ that is determined according to conventional approaches discussed above, while molecule B has a sequence representation $s^B$. The training pairs that are used in this transfer learning are $(f^A, s^B)$, and the parameters of the neural networks are updated (e.g., using a gradient updating approach) in a manner similar to the training pair (f, s) where f and s of each pair correspond to the same (i.e., identical) molecule. A result of this transfer learning as opposed to using the base model prior to the transfer learning is that given a new fingerprint, the resulting molecule defined by the sequence output in general is "better" in the aspect(s) used in the transfer learning.

Modified Latent Representations

Although the fingerprints of molecules have not been found to be suitable for comparison or manipulation directly, experimentally, the latent representations have been found to have the property that they can be arithmetically manipulated to generate new molecules.

For example, suppose molecule A has a fingerprint $f^A$ and corresponding latent representation $l^A$ and has a number of desirable properties, and unfortunately has an undesirable property. If a molecule B with fingerprint $f^B$ and latent representation $l^B$ has that undesirable property, a synthesized latent representation $l^C = l^A - l^B$ for a desired molecule C may be used as the input to the sequence generator 130 without determining the fingerprint for C.

More generally, arithmetic operations including addition, subtraction, multiplication, averaging, interpolation, etc., may be performed in the latent space to yield new molecules.

The latent space is also amenable to perturbation to yield similar molecules. For example, to generate a neighborhood of molecules similar to A, latent representations of the form $l^C = l^A + n$ for a random perturbation n (e.g., a multivariate Gaussian random vector) can be used with multiple samples of n, and each sample yielding a potentially different sequence representation $s^C$.

Conformational Properties to Sequence Generation

Although generating the sequence representation of molecule graphs from structural features based fingerprints as described above is useful, it may be even more useful to start with three-dimensional coordinates of desired features of one or more conformations of a known reference molecule or desired in a conformation of an unknown target molecule and generate molecules that match those features and locations. For example there may be between 6 and 15 feature locations for a molecule of interest. In such a representation, the set of feature types, may come, for example, from a set of 9-20 different feature types (e.g., hydrophobic, aromatic, donor, acceptor, etc.). Note that the input conformal properties may be obtained, in a manner analogous to generating a fingerprint, by processing a molecular graph of a reference molecule. However, a reference molecule is not required and the conformational properties may be determined based on desired characteristics of a potential unknown (i.e., target) molecule. Properties of a potential drug molecule may be specified by a medicinal chemist, for example, as having an aromatic ring at one location, a hydrophobic section at a second location, and a proton donor at a third location. Similarly, a three-dimensional distribution of net charge can be the basis of conformational properties. The goal is to generate one or more molecules that match such a three-dimensional specification.

It should be recognized that the specific number of features is not necessarily critical. In experiments performed using these techniques, feature counts have generally been under 20, with a majority under 15, but of course a greater number or smaller number of features can be used, and those features may be scalar values. Furthermore, the nature of the feature types is not necessarily critical. In the future, different types of feature descriptors may be developed and used in the techniques described in this document. For example, the descriptors may specify the characteristics of a larger portion of the target molecule volume and use a larger set of more specific feature types. Similarly, the features may relate to charge distribution in the target molecule.

These feature types can, for instance, be based on pharmacophores (with types such as hydrogen bond donor, acceptor, hydrophobic, aromatic, etc.), on electrostatic properties (for example the electrostatic potential specified on a grid, using a charge distribution, etc.), or on three-dimensional properties discovered by a convolutional neural network, or other type of machine-learning algorithm.

One basic approach is to replace the role of the fingerprints f in the approach described above with vector conformational property representations y of the features of the molecules. For example, if there are k locations, then y is defined by a set of tuples ($c_i$, $p_i$) where $c_i$ is from the enumerated set of features and $p_i = (p_i^{(x)}, p_i^{(y)}, p_i^{(z)})$ is a coordinate in three-dimensional (i.e., physical, x-y-z) space. A fixed-length vector representation of y may be formed, for example, by concatenating the tuples (e.g., ordered by the category) with the category $c_i$ being represented as a real value (i.e., 1.0, 2.0, etc.) or as a "one-hot" binary section, and the x, y, and z coordinates as real values. Alternatively, in order to provide rotational and translational invariance, rather than encoding the locations of the features, a set of pairwise distances (e.g., all k(k–1)/2 pairs for k locations) between the locations may be used. The vector is zero-padded (e.g., with a maximum of 20 locations). The mechanisms described above can be applied with the input to the fingerprint embedding 120 being switched from fingerprints to conformational properties. Another basic approach processes a three-dimensional spatial representations, such as a "point cloud" or image representation, for example, using convolutional neural networks or graph neural networks. Although such basic approaches can be implemented, a preferred approach described below yields significantly better results.

A number of alternative approaches use forms of three-dimensional properties, such as described in Wallach et al. "Atomnet: a deep convolutional neural network for bioactivity prediction in structure-based drug discovery," arXiv preprint arXiv:1510.02855 (2015), Axen et al. "A simple representation of three-dimensional molecular structure," Journal of medicinal chemistry, 60(17):7393-7409 (2017), or Matter et al. "Comparing 3d pharmacophore triplets and 2d fingerprints for selecting diverse compound subsets," Journal of Chemical Information and Computer Sciences, 39(6):1211-1225 (1999), may be used in place of the conformational property representation in the techniques described above.

Note that a particular molecule does not generally have a static three-dimensional conformation, therefore in this work a set of low-energy conformations are considered, and for each conformation the locations of the properties of interest are determined. Therefore, each molecule may be associated with a set of vectors y, one for each of the conformations, and in training, all the combinations of sequence descriptors and the conformational property vectors may be used. The selection of the number of such low-energy conformations that are considered may depend on the accuracy of the force-field computations and the available computational resources for determining the configurations. For example, in some examples 10 low-energy conformations may be used while in other examples 250 conformations may be used.

In a preferred approach, a feedforward neural network is constructed to map the conformational property vectors y to the previously computed latent representations l for those molecules. It is also possible to train with multiple vectors y (i.e., as separate training examples) weighted by their relative conformational energies.

The training corpus can be augmented to represent 4-tuples that include the features of the known molecules:

$$\{(f^{(n)}, s^{(n)}, l^{(n)}, y^{(n)}), n=1, \ldots, N\}. \quad (6)$$

Then, the ($l^{(n)}$, $y^{(n)}$) pairs are used to train a neural network that transforms a conformational property representation y to a latent representation l.

Training Procedure

Figure 10:
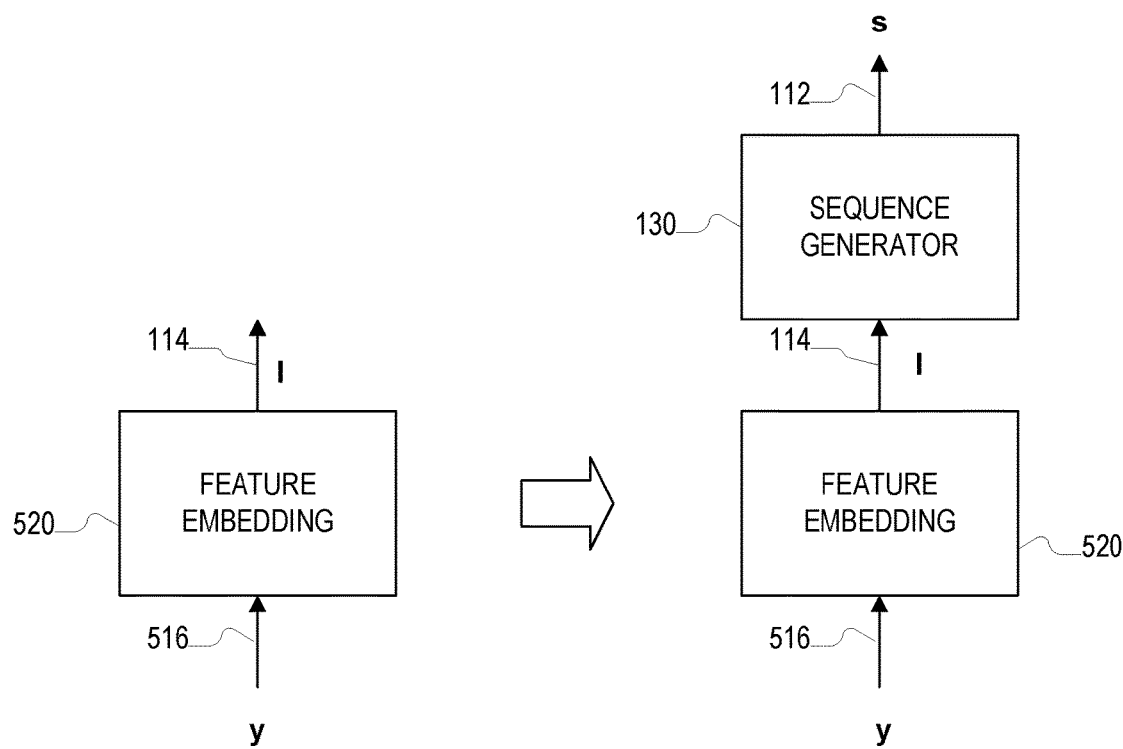
FIG. 10 is an illustration of a training process.

An additional training process (i.e., performed after training using fingerprints) can be summarized as shown in FIG. 10. That is, prior to the training using the three-dimensional features, a first training process uses the fingerprints f as input to a neural network that generates sequences s. The result of this is a first set of trained weights for the fingerprint embedding 120 that are used to map a fingerprint to a latent representation, and a second set of trained weights for the sequence generator 130 that is used in the search for the highest probability sequence representations.

Referring to FIG. 10, given the latent vectors $l^{(n)}$ for each of the molecules in the database, a feedforward neural network implementation of a feature embedding 520 is trained (e.g., again by a stochastic gradient descent procedure) so that any feature y 516 can be mapped to a corresponding latent representation l 114.

Having trained the feature embedding 520, it replaces the fingerprint embedding 120 used previously, thereby providing the complete mapping from features y 516 to sequences s 112. In some examples, the combined networks are further trained with (y, s) pairs.

Use Cases and Results

The approaches above may be used for a variety of use cases. In one use case, structural features (e.g., conformational properties) of a desired molecule are constructed according to the structural features that are desired to be represented in a resulting molecule, for example, based on examination of a set of other molecules that may have some or all of those features and may exhibit desirable chemical or biological properties. Some use cases comprise virtual screening against all of a chemical space, in which, in principle, we can access all of the possible molecules. A known set of features may exist, for example, based on a previous co-crystal structure of one small molecule bound to a receptor, or it may be generated from an apo or holo structure of a pocket of a receptor. In some use cases, the sequence of resulting molecule structures (e.g., in order of decreasing probability) is tested in sequence. This testing may include checking whether the output sequence representation indeed corresponds to a valid molecule. This testing may also include checking if the molecule is known, which may be performed computationally using a precomputed index or hash structure from the SMILES representations of a known set of molecules. The testing may also correspond to generating structural features, and comparing them (e.g., by an exact or an approximate match) with the input structural features.

In some use cases, the input is a reference molecule structure, and the goal is to generate a set of related molecules. For example, this approach can correspond to a sequence of transformations between input SMILES, to fingerprint and/or conformational properties, to latent representation, and ultimately to output SMILES.

In a set of experimental procedures used to teach the system to produce molecules that are useful in drug discovery, the system was trained on synthetically feasible molecules (i.e., drawn from the eMolecules, molPort, and SureChEMBL chemistry libraries) that were developed prior to 2017 and that had already passed a number of computational filters commonly used in drug discovery, such as removing molecules that are likely to be promiscuous, unstable, or reactive. To demonstrate that the system can generate synthesizable and nontrivially novel molecules, we showed that it recovered from their fingerprints over 94% of all molecules that passed the computational filters and were patented in 2017 or later (i.e., at a later date than molecules used in the training set).

We also demonstrated that the approach succeeds on a number of downstream drug discovery tasks. Specifically, we applied the approach to a previously published benchmark that assesses the ability of a method to modify input molecules to inhibit the dopamine receptor D2, and the system yielded a 77% lower failure rate compared to the state of the art, and yielded a 4% lower failure rate compared to the state of the art for improving so-called "molecular beauty." Furthermore, we demonstrated that the approach can successfully modify an input molecule to dock more potently against any given receptor, by further training the model using results from docking a moderately sized library of commercial molecules to the receptor. To help explain why the approach is successful in downstream discovery tasks, we analyzed an internal layer of the trained model and found that it inherits a desirable organization of chemical space from the fingerprints: Visually the layer is reminiscent of an energy landscape, with nearby basins corresponding to chemically similar molecules and vice versa. Transfer learning gradually deforms this "chemical landscape," biasing the basins to molecules better suited for the downstream drug discovery task of interest.

The neural networks described above were designed by performing a hyperparameter scan over various architectural elements and selecting the model that maximized the number of molecules in our validation set that were correctly found from their fingerprints. The validation set consisted of molecules from the SureChEMBL library that were published more recently than those in the training set, and we evaluated the final model on a test set consisting of SureChEMBL molecules published in April 2018. We found that our best single model recovered 94.1% of the validation molecules and 92.8% of the test molecules. When we trained the model with the optimal architecture on the combined training and validation sets, it recovered 94.84% of the test molecules.

A so-called "ablation" study suggests that regularization and the global optimization algorithm, A*, are key ingredients in our optimal architecture. Using the optimal architecture, we found that the top ranked molecule generated by A* was likely to exactly match the input fingerprint, and subsequent molecules generated by A* had fingerprints similar to the input fingerprint. A composite model constructed from twenty slightly different architectures recovered 97.96% of the validation set and 97.41% of the test set; adding the model trained on the combined training and validation sets, the composite model recovered 98% of the test set. For the 2% of molecules that were not recovered, the correct canonical SMILES had a very low estimated probability for all the individual models.

To gain insight into how the approach organizes chemical space, we visualized the internal chemical landscape derived from an internal layer of the neural network. The surface of the top A* solution is reminiscent of an (inverted) energy landscape in which neighboring basins contain chemically similar molecules. The surfaces of the second, third, and subsequent high-ranking solutions chosen by A* display patterns similar to those of the top solution. A molecule that is highly ranked in one region of this chemical landscape will decay to lower ranks as the distance from that region increases. Distances in the chemical landscape correlate with distances in fingerprint space. Formal tools for exploring energy landscapes have been used successfully in protein folding and in the study of atomic clusters, and related sampling methods can be used to explore models that generate molecules. We found, however, that direct transfer learning by applying additional training on specialized datasets was a simple and effective way to leverage the organization of chemical space learned by the pre-trained neural network, and so we took that approach here.

Figure 11:
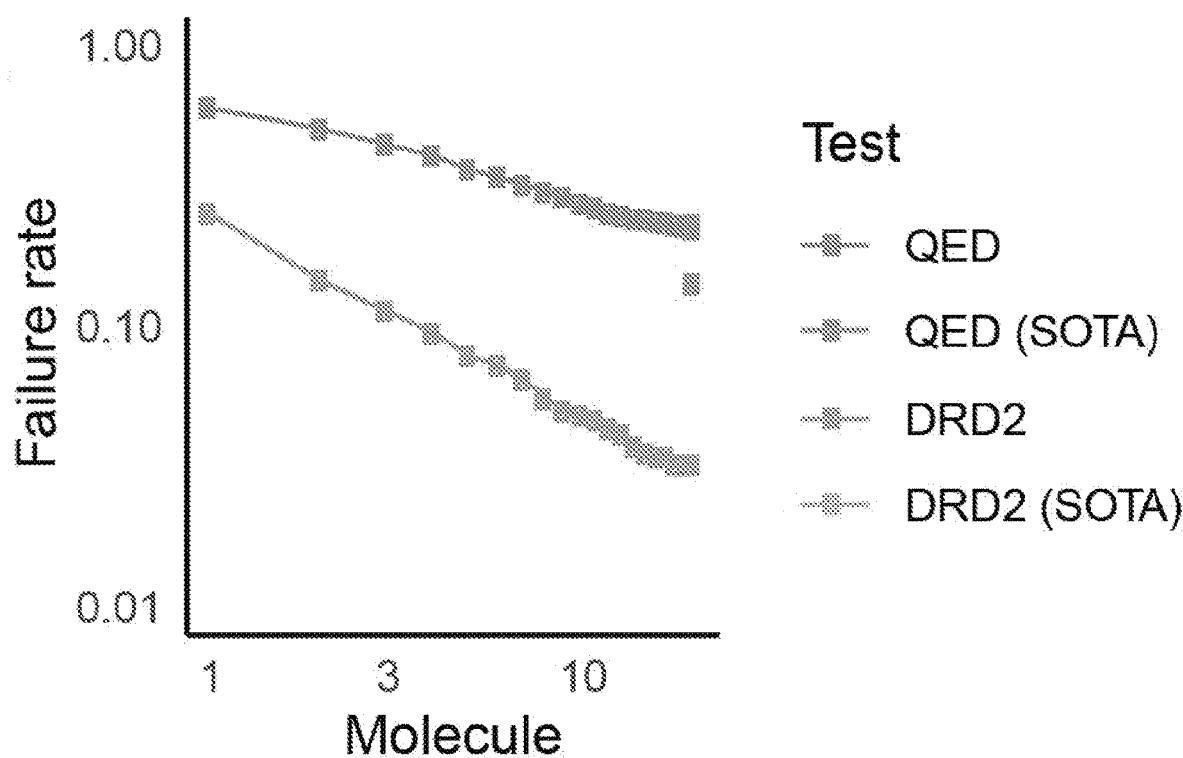
FIG. 11 is a graph of failure rate in generation of molecules.
Figure 12:
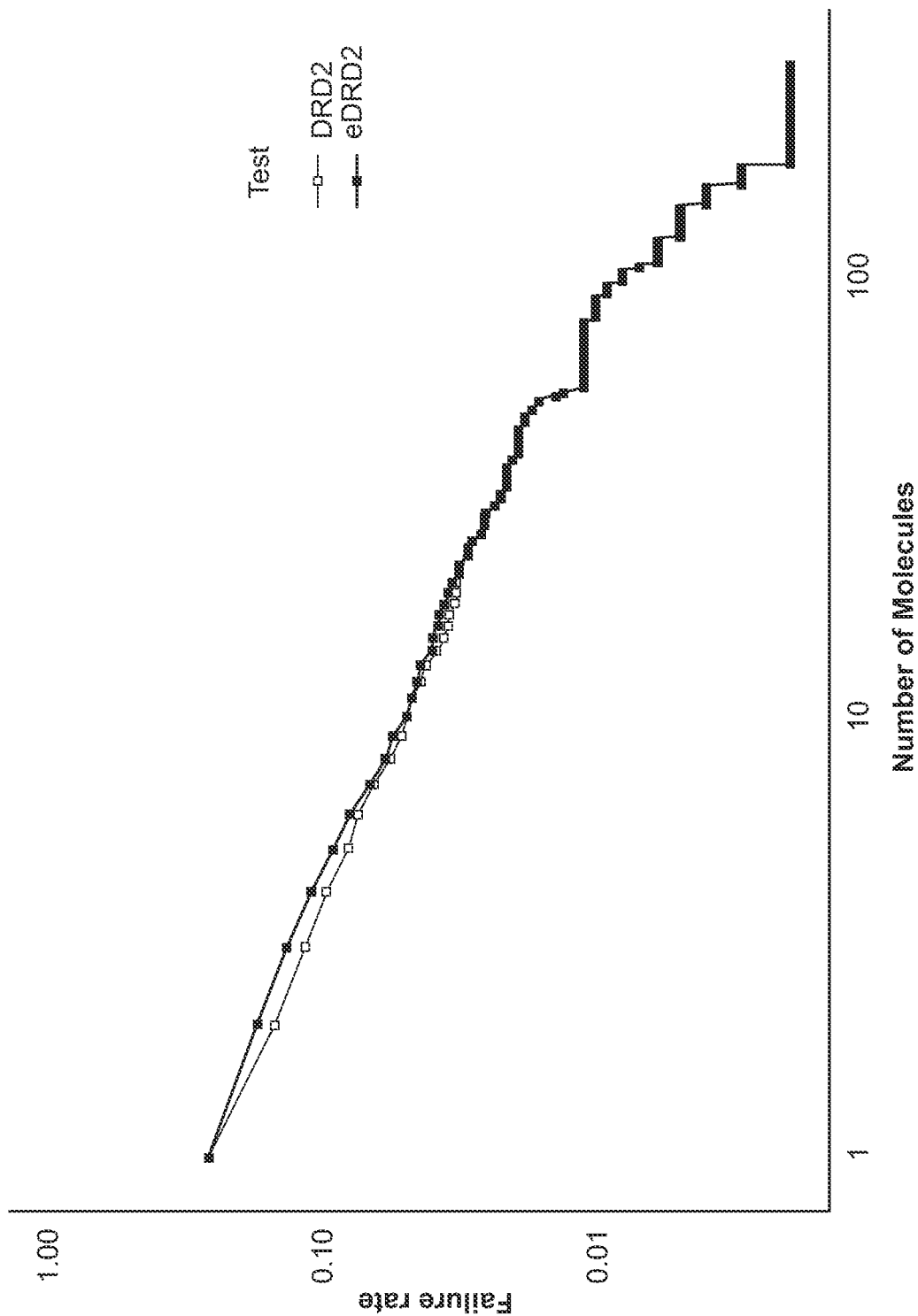
FIG. 12 is a graph of failure rate in generation of molecules.

As initial examples of the transfer learning approach, we used the system to propose inhibitors of the dopamine receptor DRD2, and to propose molecules with a high quantitative estimate of drug-likeness (QED), based on existing data. For each of these tasks, we trained the system on a dataset consisting of matched molecular pairs (pairs of similar molecules A and B, where A is the input molecule and B is the output molecule with an improved property), and evaluated the performance of the model on two benchmark metrics in comparison to five existing deep learning models and a conventional matched-pair analysis algorithm. When each model was permitted to generate twenty prospective molecules (as specified in the benchmark), the failure rate for obtaining a successful inhibitor of DRD2 was 4.4 times lower (3.2%) than with the previous state of the art, the hierarchical graph-to-graph translation method (14.4%). Our model remained better, even with only three prospective molecules, than the previous state of the art with twenty prospective molecules (see FIG. 11, which shows the failure rate to generate a better neighbor in terms of drug likeness (QED) or predicted inhibition of the dopamine receptor D2 (DRD2), as a function of the number of molecules generated from each test molecule (on a log-log scale), in comparison with the previous state of the art (SOTA) benchmarks). Using a composite system model and allowing more than twenty prospective molecules enabled us to achieve a failure rate as low as 0.2% (see FIG. 12, which shows the failure rate to take an input test molecule and generate an output stream consisting of a given number of neighboring molecules that contained a predicted inhibitor of the dopamine receptor DRD2). On the QED benchmark metric, the failure rate for producing at least one molecule (among twenty prospective molecules) with a better QED score than that of the input molecule was 4% smaller with the system (22.1%) than with hierarchical graph-to-graph translation (23.1%). The strong performance of the system on these benchmark tests suggests that the model successfully captures fundamental aspects of chemical space.

To understand why the model performed well, we examined how the pre-trained neural network parameters gradually transformed during transfer learning for the DRD2 benchmark test. We found that the internal chemical landscape deformed as the parameters changed, such that groups of similar molecules migrated together as more potent molecules were pushed up to the surface, until the majority of the local landscape was occupied by molecules predicted to be potent inhibitors of DRD2. Similar transformations occurred throughout the chemical landscape at slightly different rates, and six so-called "epochs" (passes of the DRD2 training set through the neural network) were required for optimization. The limited nature of the additional training (in terms of the number of examples and epochs, and the similarity of the matched pairs) allowed the network to keep chemically similar molecules close together while also favoring better-scoring molecules representing incremental modifications.

Figure 13:
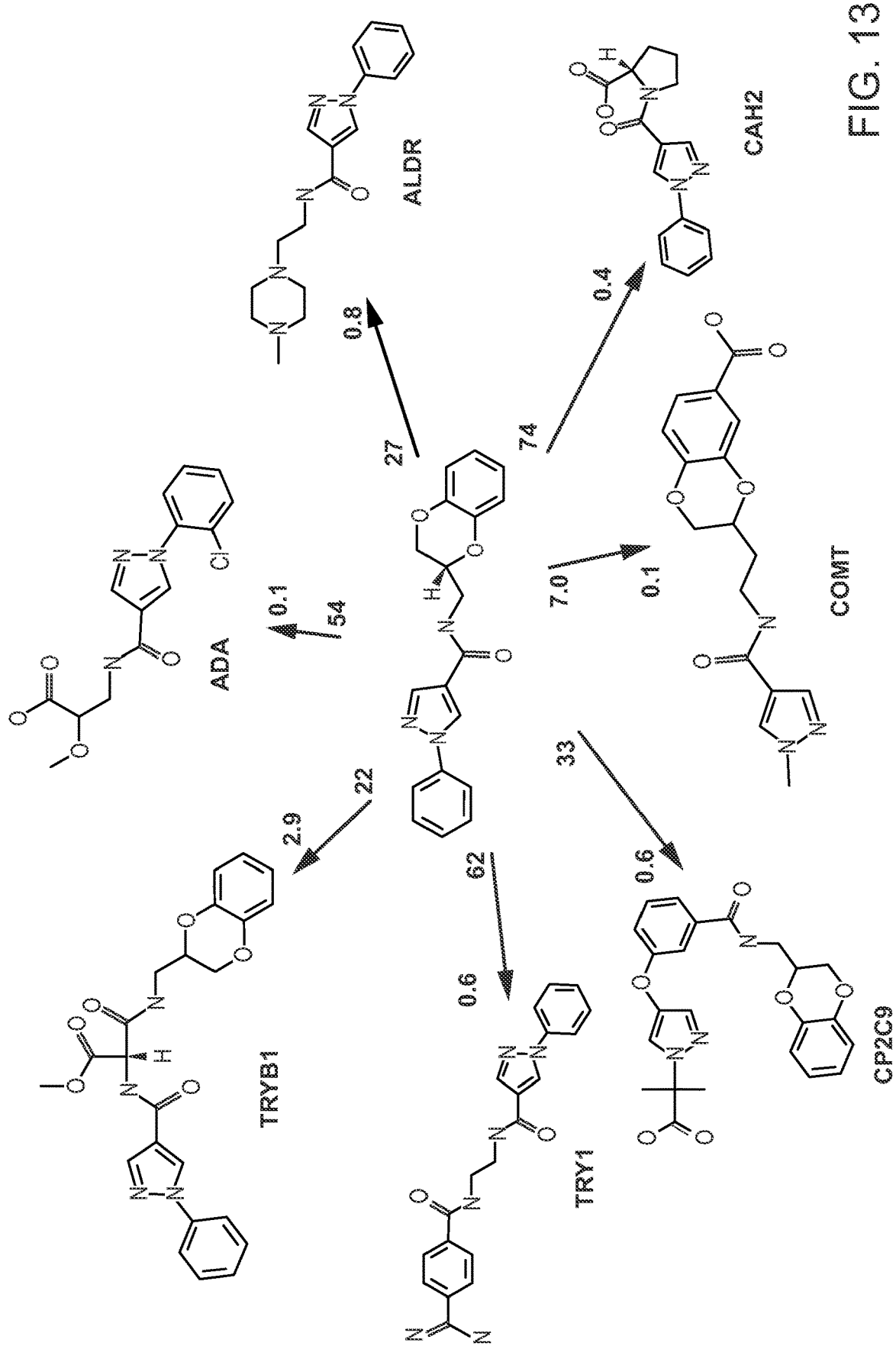
FIG. 13 is a diagram of generated neighboring molecules.

We reasoned that these reorganizations of groups of neighbors in the chemical landscape could also apply in transfer learning of other diverse small molecule properties. A frequently encountered task in drug discovery is to use a three-dimensional model of a drug target to discover new small molecules that bind to that target, and this can be viewed as a docking problem. We evaluated the ability of the approach to improve the docking scores of random scaffolds from weak binders against seven targets from the enhanced directory of useful decoys (DUD-E) (genes: ADA, ALDR, CAH2, COMT, CP2C9, TRY1, TRYB1). For each receptor, we constructed a training set by identifying matched pairs containing a potent binder and a chemically similar but weak binder from the original training set. We found that the seven resulting models each proposed neighboring molecules with significantly improved docking scores for their corresponding receptor. The modifications of the system made to the input molecule were diverse and specific to both the receptor and the input molecule (see FIG. 13, which shows a molecule from the test set and seven generated neighbors, with the arrows showing the percentile ranking of the starting molecule (at arrow bases) and the produced molecule (at arrowheads) compared to the ranking of 50,000 random molecules) and reminiscent of the way in which medicinal chemists transfer structural elements between scaffolds.

In the experiments described above, we used three collections of drug-like molecules: 1) the MolPort database of over seven million purchasable compounds (in January 2017); 2) the eMolecules database of over six million purchasable compounds (in October 2015); and 3) the SureChEMBL database of molecules extracted from the chemical literature that contained over 16 million molecules (in March 2018). All molecules were extracted in the simplified molecular-input line-entry system (SMILES) format and converted to a canonical SMILES representation using RDKit. In order to retain only drug-like molecules, we applied a number of filters to the raw data. First, we removed all molecules that contained more than 70 heavy atoms. Next, we filtered molecules that contained an atom that was not in the set H, C, N, O, F, P, S, Cl, Br, I and applied several in-house filters that removed compounds predicted to have undesirable properties, such as reactivity and mutagenicity. Finally, we used MolVS to remove salts, by selecting the largest fragment, and to neutralize the molecules.

We tokenized the SMILES with SentencePiece using the byte-pair-encoding (BPE) algorithm, keeping 4 tokens (<begin>, <forward>, <reversed>, and <end>) for the start, left-to-right direction, right-to-left direction, and end of a SMILES string. The total number of tokens is a hyperparameter; after measuring the recovery of molecules from the validation set using 2,000, 4,000, and 8,000 tokens, we decided to use 8,000 tokens. With this choice 99.96% of the training molecules could be represented by strings of 27 or fewer tokens (the 5th, 50th, and 95th percentiles had 6, 9, and 14 tokens respectively). We removed all SMILES strings that consisted of more than 27 tokens.

Fingerprints were constructed as concatenations ECFP4 and ECFP6 fingerprints. The ECFP4 and ECFP6 fingerprints are computed using RDKit and include chirality bits. Both fingerprints use 2,048 bits, such that the total input to the model is 4,096 bits. The percentage of training molecules with 4,096 bits exactly matching another training molecule was 0.12%.

We trained the model with the Adam optimizer using the "1 cycle" learning rate and momentum schedule. Gradient norms were clipped at 0.3. We considered three hyperparameters concerning that training schedule: the number of epochs, the maximum learning rate, and the so-called "dividing factor." The initial learning rate is calculated by dividing the maximum learning rate by the dividing factor. The final learning rate is calculated by dividing the initial learning rate by the square of the dividing factor. During the first 49% of the training schedule, the learning rate increases linearly from the initial learning rate to the maximum learning rate while the momentum decreases linearly from 0.8 to 0.6. Over the next 49% of the training schedule, the learning rate decreases linearly from the maximum learning rate to the initial learning rate, while the momentum increases linearly from 0.6 to 0.8. In the last 1% of training, the momentum is fixed at 0.8, while the learning rate decreases linearly from the initial learning rate to the final learning rate. To train DESMILES, we used a dividing factor of 10. We chose the maximum learning rate and number of epochs using a grid search, with performance evaluated on a validation set. The optimal hyperparameters were 128 epochs and a maximum learning rate of $10^{-3}$. This corresponds to an initial learning rate of $10^{-4}$ and a final learning rate of $10^{-6}$.

We "recovered" a molecule when the fingerprint of the generated molecule exactly matched the input fingerprint. We found that in 1.04% of the test molecules, the first generated molecule that recovered the fingerprint had a different small molecule graph; typically the system also generated the exact input molecule further down in the stream of generated molecules, except for 0.06% of molecules (six out of 10,000), which it did not generate within our typical fixed compute time.

In order to be useful as a tool in drug discovery, an algorithm should be able to generalize beyond the areas of chemical space that it has seen. We hypothesized that a random split of the data would be insufficient to measure the ability of the approach to generalize to new areas of chemical space, since many molecules in the test set would be close neighbors of molecules in the training set, and we thus constructed a validation set using a temporal split. We constructed the training set from MolPort,34 eMolecules, and SureChEMBL molecules published before 2017. The validation set consists of a random subset of 10,000 molecules from SureChEMBL published between Jan. 1, 2017 and Jan. 16, 2018. The test set consists of a random subset of 10,000 molecules published by SureChEMBL in April of 2018. During the initial development of the system architecture, we used a random 80% subset of the training set and tested the performance of our best model using the remaining 20% of the training set (finding it recovered 99.72% of these molecules). Finally, we trained a model with the optimal architecture on the full training set.

As introduced above, in some uses, the system takes as input the fingerprint of an existing molecule and generates new molecules that (1) were reasonably similar to the starting molecule as specified by a similarity threshold using the Tanimoto similarity to the ECFP4 fingerprint of the molecules and (2) have an improved property (e.g., better predicted biological activity against the dopamine type 2 receptor, DRD2). In one experiment, this was accomplished by assembling a new specialized training set consisting of pairs of molecules, such that the second molecule of each pair satisfied conditions (1) and (2). We then fine-tuned the pre-trained network by additional training on this set, effectively asking the network to write the SMILES of the second molecule in the pair, given the fingerprint of the first. We used the training, validation, and test sets provided in Jin et al. "Learning multimodal graph-to-graph translation for molecular optimization," arXiv preprint arXiv:1812.01070 (2018), and used the "1 cycle" learning rate and momentum schedule described above. We tested the performance on the validation set of 50 random combinations of three hyperparameters: We picked between five and twelve epochs (inclusive), a maximum learning rate from the set 0.002, 0.001, 0.0005, and a dividing factor between five and ten (inclusive). We performed a grid search around the most promising combination of hyperparameters and selected the best-performing parameters for evaluation of the test set.

We first found the best-performing hyperparameters for testing biological activity against DRD2. For this test, we found that the optimal hyperparameters were six epochs, a maximum learning rate of 0.001, and a dividing factor of seven. We next selected hyperparameters for testing the quantitative estimate of drug-likeness (QED). For this test, we found that the optimal hyperparameters were nine epochs, a maximum learning rate of 0.0005, and a dividing factor of eight. Finally, we selected hyperparameters for testing the penalized octanol-water partition coefficient (log P). For the Log P test with a similarity constraint of 0.6, the optimal hyperparameters were 10 epochs, a maximum learning rate of 0.0005, and a dividing factor of 10. For the Log P test with a similarity constraint of 0.4, the optimal hyperparameters were five epochs, a maximum learning rate of 0.0005, and a dividing factor of six. For each molecule in the test set, the system generated 20 molecules using the A* algorithm described above. Details of how performance is measured can be found in the paper by Jin et al.

We fine-tuned the system to generate a set of molecules with improved docking scores for each of seven different receptors: ADA, ALDR, CAH2, COMT, CP2C9, TRY1, and TRYB1. We performed all docking using an in-house method. We generated training pairs from the original training set, excluding all molecules in the DUD-E set for each receptor, as follows. 1) We randomly selected 50,000 molecules and docked them. 2) We took the top 5% of molecules and, for each of them, found up to 50 molecules with an ECFP4 similarity of at least 0.4. 3) We docked those additional molecules and kept only those with a docking score weaker than their parent molecule by a determined threshold. A threshold of 30 units was used for CP2C9, TRY1 and TRYB1. A threshold of 60 units was used for ADA, ALDR, CAH2, and COMT in order to keep the number of training pairs comparable between the seven receptors. For the transfer learning, we used the hyperparameters chosen for the DRD2 experiment as above. We evaluated the fine-tuned the system using the molecules from the DRD2 validation set: For each molecule, the system generated 20 candidate molecules. All generated molecules with an ECFP4 similarity of at least 0.4 to the starting molecule were docked against the corresponding receptor.

Alternatives and Implementations

It should be understood that the specific system configurations, for example, as shown in FIGS. 3 and 4 are only examples. For instance, other sequence generating structures may be used with other forms of recurrent networks.

As discussed above, a variety of inputs can be used to generate molecular graphs, alone or in combination, including but not limited to 1. a fingerprint computed (e.g., by rules) from a reference molecule,
2. conformational properties computed from a reference molecule, either from one conformation of the molecule or from a set of conformations of the reference molecule,
3. a combination of 1, and 2, or
4. conformational properties determined without use of a particular reference molecule, but representing properties of a desired target molecule.

In a number of cases, the latent representation computed from the input is used directly. In other cases, the latent representation is modified, for example by perturbation or by combination of latent representations with different inputs. The output of the sequence generation can include a single sequence (i.e., a single molecular graph), or a series of sequences, where the generation of the sequences may be terminated when a predetermined number of sequences is generated, or when one of more sequences satisfy certain conditions. Conditions that may be tested for output sequences may include one or more of the following:
1. representation of a valid molecule (e.g., the output corresponds to a valid SMILES string),
2. exact match of a fingerprint of an output sequence to an input fingerprint
3. exact or approximate or partial match of conformational properties of an output molecular graph and input conformational properties.

Further evaluation of output molecular graphs may include one or more of the following:
1. computer-implemented molecular dynamics simulation,
2. computer-implemented docking evaluation,
3. free energy calculation, for example, to characterize expected binding behavior,
4. expert evaluation,
5. physical synthesis, for example, based on a known synthesis procedure, based on a computer-determined synthesis procedure, or based on a synthesis procedure determined by a skilled chemist, and
6. evaluation of the synthesized molecule in chemical and/or biological experiments.

In some use cases an iterative approach may be used such that an output set of molecular graphs is expanded by using each of the output molecular graphs as an input to the system, and the union of the outputs is used as a "second generation" mapping from the original input. Such an iteration may be repeated for multiple generations to yield an even larger set of resulting molecular graphs, which may then be evaluated using the techniques enumerated above. In some use cases, the output molecular graphs (from one or more generations) may be used in other search techniques, for example, forming a domain for a Monte Carlo search or optimization approach.

Embodiments of the approaches described above may be implemented in software, with instructions stored on a non-transitory machine-readable medium that cause a data processing system to perform the described procedures. The data processing system may use conventional general-purpose processors, or special-purpose processors, for example, tailored to the computational requirements of the methods. For example, some aspects (e.g., training) may be implemented using graphical processing units (GPU). In some embodiments, special-purpose hardware may be used to implement one or more aspects of the method.

One or more embodiments described in this document are within the scope of the appended claims.

What is claimed is:

1. A computer-implemented method for generating a molecular graph comprising:
   obtaining a data representation of first structural features of a first molecule;
   processing, using a computer, the data representation of the first structural features of the first molecule to yield a first latent representation of the first molecule; and
   processing, using the computer, the first latent representation to yield a data representation of a molecular graph of at least one molecule matching the first structural features;
   wherein the first structural features comprises conformational properties of a conformation of a molecule.

2. The method of claim 1, further comprising providing the molecular graph of the at least one molecule for evaluation of chemical or biological properties of said at least one molecule.

3. The method of claim 2, further comprising evaluating a molecule represented by the molecular graph by at least one of:
   (a) computer-implemented molecular dynamics simulation,
   (b) computer-implemented docking evaluation,
   (c) free energy calculation to characterize expected binding behavior,
   (d) physical synthesis based on a known synthesis procedure or based on a computer-determined synthesis procedure, and
   (e) evaluation of the molecule in chemical or biological experiments.

4. The method of claim 1, wherein the first molecule is a known reference molecule.

5. The method of claim 1, wherein obtaining the data representation of the first structural features includes processing a data representation of a first molecular graph to yield the first structural features.

6. The method of claim 5, wherein processing the data representation of the first molecular graph comprises applying a plurality of rules to yield the first structural features.

7. The method of claim 1, wherein the first molecule is an unknown target molecule.

8. The method of claim 1, wherein the data representation of the molecular graph of the at least one molecule comprises a linear symbolic representation.

9. The method of claim 8, wherein the linear symbolic representation corresponds to a SMILES representation.

10. The method of claim 8, wherein the linear symbolic representation comprises symbols each representing at least some individual atoms and symbols each representing a group of bonded atoms.

11. The method of claim 8, wherein the linear symbolic representation comprises a compression of the SMILES representation.

12. The method of claim 1, wherein the conformational properties are determined for a known reference molecule.

13. The method of claim 1, wherein the conformational properties are determined as desired in an unknown target molecule.

14. The method of claim 1, wherein the representation of conformational properties comprises features tied to three-dimensional locations of those attributes in a conformation of a molecule.

15. The method of claim 14, wherein the conformational properties comprise a set of locations and discrete categories of features of a molecule at said locations.

16. The method of claim 14 wherein the conformational properties comprise properties of a plurality of low-energy conformations of a molecule.

17. The method of claim 1, wherein processing the data representation of the first structural features to yield the first latent representation comprises using a first artificial neural network.

18. The method of claim 1, wherein processing the first latent representation to yield the data representation of the molecular graph of at least one molecule matching the first structural features comprises processing the latent representation using a second artificial neural network to yield a sequence representation of the at least one molecule matching the structural features.

19. The method of claim 1, wherein the first structural features comprise a fingerprint determined from a molecular graph.

20. The method of claim 19, wherein the fingerprint comprises a fixed length binary vector.

21. The method of claim 20, wherein the fingerprint representation comprises an extended connectivity fingerprint.

22. The method of claim 19 wherein the fingerprint representation is encoded to a continuous vector.

23. The method of claim 1, wherein the molecular graph of the at least one molecule has the first structural features.

24. A computer-implemented method for generating a molecular graph comprising:
obtaining a data representation of first structural features of a first molecule;
processing, using a computer, the data representation of the first structural features of the first molecule to yield a first latent representation of the first molecule; and
processing, using the computer, the first latent representation to yield a data representation of a molecular graph of at least one molecule matching the first structural features;
wherein processing the first latent representation to yield the data representation of the molecular graph of at least one molecule matching the first structural features comprises processing the latent representation using a second artificial neural network to yield a sequence representation of the at least one molecule matching the structural features; and
wherein processing the latent representation to yield a sequence representation of the at least one molecule matching the structural features comprises processing the latent representation to yield a plurality of sequence representations, determining structural features for each representation of said plurality of sequence representations, and comparing the determined structural features to determine a match of the determined structural features to the first structural features.

25. The method of claim 24, wherein processing the latent representation to yield the plurality of sequence representations includes generating a first sequence representation, and wherein generating the first sequence representation includes generating successive distributions of next symbols in the sequence representation using the latent representation as an input to a second artificial neural network and searching possible sequences using the successive distributions to yield one or more best sequences.

26. The method of claim 25, wherein generating the distribution of a next symbol includes using the latent representation and a prefix of the next symbol in the sequence as input to the second artificial neural network.

27. The method of claim 25, wherein searching the possible sequences comprises performing an A-star search procedure.

28. A computer-implemented method of training a neural network for generating a molecular graph comprising:
obtaining a first set of molecular graphs;
processing each molecular graph of the first set of molecular graphs to determine respective sequence representations;
processing each molecular graph of the first set of molecular graphs to determine respective structural features; and
training, using the structural features and respective sequence representations, a combination of a first neural network and a second neural network;
wherein the first neural network implements a transformation from the structural features to a latent feature representation, and the second neural network implements a transformation from the latent feature representation to a sequence representation.

29. The method of claim 28 wherein the structural features comprise fingerprints.

30. The method of claim 28, further comprising:
obtaining a second set of molecular graphs;
processing each molecular graph of the second set of molecular graphs to determine respective latent representations; and
processing each molecular graph of the second set of molecular graphs to determine respective conformational properties;
training, using the latent representations and the conformational properties, a third neural network;
wherein the third neural network implements a transformation from conformational properties to a corresponding latent representation; and
wherein a combination of the third neural network and the second neural network together implement a transformation from conformational properties to a sequence representation of a molecular graph.

31. The method of claim 28, further comprising:
obtaining a set of pairs of molecular graphs, each pair having a first molecular graph and a second molecular graph, the second molecular graph representing a second molecule having a different degree of a property than a first molecule represented by the first molecular graph;
processing the first molecular graphs to determine corresponding first structural features; and
applying a transfer learning procedure to at least the second neural network using the pairs of first structural features and second molecular graphs.

* * * * *